(12) United States Patent
Seto et al.

(10) Patent No.: US 6,689,074 B2
(45) Date of Patent: Feb. 10, 2004

(54) WEARABLE MUSCULAR-FORCE SUPPLEMENTING DEVICE

(75) Inventors: Takeshi Seto, Chofu (JP); Kunihiko Takagi, Shimosuwa-machi (JP)

(73) Assignee: Seiko Epson Corporation, Tokyo (JP)

( * ) Notice: Subject to any disclaimer, the term of this patent is extended or adjusted under 35 U.S.C. 154(b) by 238 days.

(21) Appl. No.: 09/788,602

(22) Filed: Feb. 21, 2001

(65) Prior Publication Data

US 2001/0029343 A1 Oct. 11, 2001

(30) Foreign Application Priority Data

| Mar. 28, 2000 | (JP) | ................................. 2000-089584 |
| Mar. 29, 2000 | (JP) | ................................. 2000-092503 |
| Apr. 6, 2000 | (JP) | ................................. 2000-104969 |

(51) Int. Cl.[7] ............... A61H 1/02; B25J 17/00; B25J 9/10; B25J 9/16
(52) U.S. Cl. ............... 601/5; 601/33; 623/24; 623/26; 901/46; 901/48
(58) Field of Search ............... 601/5, 23, 33, 601/34, 35, 40; 623/24, 25, 26; 901/46, 48, 49; 482/45, 46

(56) References Cited

U.S. PATENT DOCUMENTS

| 3,631,542 A | * | 1/1972 | Potter | ............... 623/25 |
| 3,799,159 A |   | 3/1974 | Scott  |                    |
| 4,442,387 A | * | 4/1984 | Lindbom | ............... 901/17 |
| 5,282,460 A |   | 2/1994 | Boldt  |                    |
| 5,383,939 A | * | 1/1995 | James  | ............... 623/24 |
| 5,611,764 A | * | 3/1997 | Bonutti et al. | ...... 601/33 |
| 5,647,554 A | * | 7/1997 | Ikegami et al. | ...... 901/1 |
| 5,672,044 A | * | 9/1997 | Lemelson | ......... 901/1 |
| 5,865,770 A | * | 2/1999 | Schectman | ....... 601/23 |
| 6,312,400 B1 | * | 11/2001 | Itikawa et al. | ..... 601/100 |

FOREIGN PATENT DOCUMENTS

| GB | 2 260 495 A | 4/1993 |
| WO | WO 94/09727 | 5/1994 |

* cited by examiner

Primary Examiner—Danton D. DeMille
(74) Attorney, Agent, or Firm—Oliff & Berridge, PLC

(57) ABSTRACT

A muscular-force supplementing device of the present invention includes an artificial muscular-force generating section and a control section that controls the driving of the artificial muscular-force generating section. The artificial muscular-force generating section includes a pair of mounting portions worn at two positions on both sides of a wrist joint of the user, and an actuator hinged on connecting portions of the mounting portions. The actuator is a device having therein a plurality of hydraulic cylinders to be operated in a dual-stroke manner. When hydraulic oil serving as the fluid is supplied to pressure chambers, a pair of piston rods are extended, and linear actuator force is transmitted to the connecting portions of the mounting portions, thereby transmitting bending force to the joint of the user.

31 Claims, 12 Drawing Sheets

WEARABLE MUSCULAR-FORCE SUPPLEMENTING DEVICE

BACKGROUND OF THE INVENTION

1. Field of Invention

The present invention relates to a wearable muscular-force supplementing device to be worn at joints of the wrist, arm, knee, and the like of a user so as to generate supplementary muscular force.

2. Description of Related Art

Conventional wearable muscular-force supplementing devices are disclosed in, for example, Japanese Unexamined Patent Application Publication No. 7-163607 (hereinafter referred to as a "first conventional art") and Japanese Unexamined Utility Model Application Publication No. 5-39518 (hereinafter referred to as a "second conventional art").

The first conventional art includes a thigh-worn portion to be worn on the thigh of a user, a shank-worn portion to be worn on the shank, power transmission arms fixed to the thigh-worn portion and the shank-worn portion at one end and connected to each other at the other end at a knee joint so as to bend and straighten the joint, a driving section using an electromotor for applying power for bending and straightening to the power transmission arms, and a power-source and control section for the electromotor and driving section. The power-source and control section is worn on the body of the user. In the driving section, a joint shaft connected to the power transmission arms rotates together with one of the power transmission arms. A gear mounted on an output shaft of the electromotor is meshed with a gear mounted on the joint shaft, and power transmission is enabled and disenabled between the gear of the joint shaft and the joint shaft via a clutch.

The first conventional art makes it possible to assist persons having low muscular strength in the legs, persons of advanced age, and the like in the climbing of stairs.

The second conventional art includes a shoulder-fixed member to be supported on the front side of the shoulder of a disabled arm, and an upper-arm-fixed member and a forearm-fixed member, respectively supported on the upper arm and the forearm. The upper-arm-fixed member and the forearm-fixed member are connected at the elbow, and an artificial rubber muscle is extended between the shoulder-fixed member and the forearm-fixed member so as to be expanded an contracted in response to changes in the internal air pressure thereof.

According to the second conventional art, a special electronic circuit (controller) and the like are unnecessary, and the range of movement can be easily set by utilizing the spring characteristics of the artificial rubber muscle in accordance with air pressure and contraction efficiency corresponding thereto.

However, the first conventional art has the following problems:

(1) While power transmission is enabled and disabled by the clutch, for example, when a user climbing the stairs, and the user is going to fall down while power is being transmitted, the clutch cannot be quickly disengaged. In this case, even if the user, who is going to fall down, desires to quickly assume a recovery attitude, the user cannot freely move the legs and may be placed into a dangerous situation because the clutch is engaged.

(2) Since supplementary muscular force is automatically generated in response to a specific attitude of the user, the user cannot do anything else except remove the device when supplementary muscular force is unnecessary.

(3) In order to change the power of the supplementary muscular force as the user desires, it is necessary to change the output of the electromotor in the driving section. For this reason, a high-output electromotor must be used to respond to increases and decreases in the power of supplementary muscular force. This increases the size of the device.

(4) A heavy power source must be worn on the body of the user, and this may limit the motion of the user. While a myoelectric sensor is used to check the muscular force of the user, mounting of the myoelectric sensor is troublesome, and inflammation of the skin is sometimes caused due to adhesive tape or the like used to hold the sensor on the skin.

(5) For example, when the device is worn on the body in winter, cold instruments are in contact with the skin, and the user feels cold and uncomfortable.

In contrast, the second conventional art also has the following problems:

(6) Even when the user, who is going to fall down, desires to quickly assume a recovery attitude, he or she cannot support the entirety of the body because the arm is restrained. This may lead to a dangerous situation.

(7) Since the artificial rubber muscle has only a single pressure chamber, when the pressure chamber is ruptured, supplementary muscular force is suddenly lost. In a case in which supplementary muscular force is suddenly lost while the user is carrying something heavy, the body of the user may be injured.

(8) Artificial rubber muscles may be arranged in parallel in order to increase the power of supplementary muscular force. When a plurality of artificial rubber muscles are thus arranged, the number of external tubes to be connected thereto is increased, and therefore, it is troublesome to handle the external tubes so that they do not become entangled.

(9) The artificial rubber muscle is stiffened and contracted by pressure, thereby bending the arm of the user. Since the contracted artificial rubber muscle lies in the bending direction of the arm of the user, however, it reduces the range of movement of the arm of the user.

(10) Since the artificial rubber muscle serving as an actuator is not in close contact with the body, problems occur; for example, a portion of clothing (a shirt or a coat) becomes entangled therein. Furthermore, when the user wears the device over a shirt, he or she cannot wear a jacket thereover.

(11) In a manner similar to that in the first conventional art, when the device is worn on the body in winter, the user feels cold and uncomfortable.

SUMMARY OF THE INVENTION

An object of the present invention is to provide a wearable muscular-force supplementing device which is easily handled with a fail-safe mechanism for the body of a user, for example, which immediately stops generation of supplementary muscular force in the case of an emergency and prevents generated force from being suddenly reduced even when an actuator breaks, which is easily wearable with the actuator not protruding from a joint of the user, which is so compact as not to reduce the range of movement of the joint of the user, which is so light in weight that it does not restrain the movement of the user, and which does not cause the user to feel uncomfortable, such as feel cold, when wearing the device.

A wearable muscular-force supplementing device according to an aspect of the present invention includes an artificial muscular-force generator that applies supplementary muscular force for bending to a joint of a user, and a controller that controls the driving of the artificial muscular-force generator, wherein the controller has an artificial muscular-force releasing device that releases the joint from restraint by stopping generation of supplementary muscular force by the artificial muscular-force generator.

According to this invention, when the user assumes a dangerous attitude, for example, when the user is going to fall down, generation of supplementary muscular force in the artificial muscular-force generator is stopped, and therefore, the user can freely move the body without any restraint from the artificial muscular-force generator.

Preferably, the artificial muscular-force releasing device has a sensor that detects the attitude of the user, and a release controller that stops generation of supplementary muscular force by the artificial muscular-force generator when determining, based on information detected by the sensor, that the user is in a dangerous attitude, for example, indicating that the user is going to fall down.

In this case, the sensor detects a dangerous position, for example, a state in which the user is going to fall down. The release controller can stop generation of supplementary muscular force by the artificial muscular-force generator based on information detected by the sensor.

The controller may have a voice input device, and may control generation of supplementary muscular force to be applied to the joint by the artificial muscular-force generator or may exert control so as to operate the artificial muscular-force releasing device, based on voice input from the voice input device.

In this case, supplementary muscular force is generated in the artificial muscular-force generator when the user says "Start", and the generation of supplementary muscular force by the artificial muscular-force generator is stopped when the user says "Stop". When the user says "Danger", the artificial muscular-force releasing device is operated to release the joint from restraint.

The artificial muscular-force generator may have a fluid-pressure type actuator, and the controller may include a reservoir that stores fluid, a fluid feeding device that pressurizes and transfers the fluid received from the reservoir to the actuator, and a feeding-drive control device that controls the fluid feeding device. The artificial muscular-force releasing device may have a control valve interposed in a fluid path communicating with the actuator and connected to the reservoir while detouring around the fluid feeding device, and the release controller may have an opening control section that controls the opening of the control valve.

In this case, when the release controller detects, from an acceleration sensor, a dangerous attitude of the user, for example, a state in which the user is going to fall down, it exerts control so as to open the control valve. Thereby, the fluid in the actuator is fed back to the reservoir, and generation of supplementary muscular force by the artificial muscular-force generator can be stopped.

A wearable muscular-force supplementing device according to another aspect of the present invention includes an artificial muscular-force generator that applies supplementary muscular force for bending to a joint of a user, and a controller that controls the driving of the artificial muscular-force generator, wherein the controller has a generated-force stabilizer that inhibits force generated by the artificial muscular-force generator from being reduced due to breakage.

In this case, even when an actuator breaks while the user is carrying something heavy, the generated-force stabilizer prevents force generated by the actuator from being suddenly reduced. Therefore, the body of the user will not be injured.

The artificial muscular-force generator may include a fluid-pressure type actuator having a plurality of pressure chambers, and the generated-force stabilizer may separate the pressure chambers.

In this case, even when the actuator is partly broken, since the generated-force stabilizer separates the broken pressure chamber, force generated by the actuator can be prevented from being suddenly reduced.

The controller may include a reservoir that stores fluid, a fluid feeding device that pressurizes and transfers the fluid received from the reservoir to the actuator, and a feeding-drive control device that controls the fluid feeding device. The generated-force stabilizer may include a pressure sensor that detects the pressures in the pressure chambers, control valves interposed in a plurality of flow paths connected between the fluid feeding device and the pressure chambers of the actuator, and a generated-force stabilization control section that closes a control valve connected to a given pressure chamber when it is determined based on information detected by the pressure sensor that the pressure in the pressure chamber has decreased.

In this case, the pressure sensor detects that a given pressure chamber of the actuator is in an abnormal condition. The generated-force stabilization control section closes a control valve connected to the given pressure chamber. Since the broken pressure chamber is thereby separated, the force generated by the actuator will not be suddenly reduced.

A wearable muscular-force supplementing device according to a further aspect of the present invention includes an artificial muscular-force generator that applies supplementary muscular force for bending to a joint of a user, and a controller that controls the driving of the artificial muscular-force generator, wherein the artificial muscular-force generator is electrically driven, there are two power sources, a main power source and an auxiliary power source, the main power source and the auxiliary power source are connected to a power switching device, and the power switching device performs switching so as to supply power from the auxiliary power source for a predetermined time when power supply from the main power source is stopped.

In this case, since power is supplied from the auxiliary power source when supply from the main power source is stopped, it is possible to avoid the danger of a sudden stop of generation of supplementary muscular force.

The power switching device may have an alarm device for sounding an alarm when power supply from the auxiliary power source is started.

This makes it possible to reliably inform the user that power supply from the main power source has stopped.

A wearable muscular-force supplementing device according to a further aspect of the present invention includes an artificial muscular-force generator that applies supplementary muscular force for bending to a joint of a user, and a controller that controls the driving of the artificial muscular-force generator, wherein the artificial muscular-force generator has a pair of mounting portions to be worn at two positions on the body of the user on both sides of the joint, and an actuator connected between the mounting portions, and the actuator has a restraint that prevents excessive supplementary muscular force from being applied to the joint of the user.

In this case, the joint will not be damaged by excessive supplementary muscular force. As the restraint, the mounting portions may be provided with stopper members placed opposed to each other so that the positions thereof are adjustable and so that the stopper members contact before excessive supplementary muscular force is applied to the joint of the user. As the restraint, a variable-length elastic belt may be connected between the mounting portions so that the force of the actuator is stopped by tension generated by the elastic belt before excessive supplementary muscular force is applied to the joint of the user.

This makes it possible to prevent, by a mechanical structure, the joint from bending excessively.

A wearable muscular-force supplementing device according to a further aspect of the present invention includes an artificial muscular-force generator that applies supplementary muscular force for bending to a joint of a user, and a controller that controls the driving of the artificial muscular-force generator, wherein the artificial muscular-force generator has a pair of mounting portions to be worn at two positions on the body of the user on both sides of the joint, and an actuator connected between the mounting portions, the actuator includes a plurality of actuator divisions arranged in parallel and connected to one another between the mounting portions, the mounting portions have detachably connecting portions that detachably connect the actuator divisions thereto, and a predetermined number of actuator divisions are connected to the detachably connecting portions of the mounting portions in accordance with a desired power of supplementary muscular force.

In this case, since actuator force can be changed only by connecting a predetermined number of actuator divisions to the detachably connecting portions of the first and second mounting portions, it is possible to freely set the power of supplementary muscular force as the user desires. By detaching the actuator divisions connected to the detachably connecting portions of the first and second mounting portions, the artificial muscular-force generator can be made compact.

The actuator divisions may be formed of fluid-pressure type actuators each having a pressure chamber therein, and the detachably connecting portions of the mounting portions may also serve as fluid transfer connectors to transfer fluid serving as working fluid into and out of the pressure chambers of the actuator divisions.

In this case, the tubes and the like for supplying fluid are not exposed outside the device, and the artificial muscular-force generator can be handled easily.

A wearable muscular-force supplementing device according to a further aspect of the present invention includes an artificial muscular-force generator that applies supplementary muscular force for bending to a joint of a user, and a controller that controls the driving of the artificial muscular-force generator, wherein the artificial muscular-force generator has an actuator serving as a fluid chamber having a pressure chamber, and the controller includes a fluid transfer control section that controls transfer of the fluid with respect to the actuator, and at least one of the actuator and the fluid transfer control section has a fluid discharge control section that discharges internal fluid to the outside.

In this case, when the fluid is a liquid, such as hydraulic oil, the weight of the device is reduced by discharging at least one of the fluid in the actuator and the fluid in the fluid transfer control section to the outside by the fluid discharge control section. This facilitates an operation of transporting the device in a non-operation state.

The fluid discharge control section may have a leakage alarm that detects leakage of the fluid and sounds an alarm when discharge of the fluid out of at least the actuator and the fluid transfer control section is stopped.

This makes it possible to allow the user to immediately ascertain that an abnormal condition exists in which fluid is leaking to the outside.

The controller may include a fluid supply control section capable of supplying the fluid from the outside to at least one of the actuator and the fluid transfer control section, and a filter placed at an inlet of the fluid supply control section so as to remove foreign matters mixed in the fluid. In this case, the filter removes impurities, such as dust, mixed in the fluid. For this reason, since the fluid transfer control section feeds and feeds back the fluid having no impurities, it is possible to substantially reduce problems resulting from impurities.

A wearable muscular-force supplementing device according to a further aspect of the present invention includes an artificial muscular-force generator that applies supplementary muscular force for bending to a joint of a user, and a controller that controls the driving of the artificial muscular-force generator, wherein the controller is driven by power from an external power source, and has a power cord to be connected to the external power source, and a cord reel that winds up the power cord thereon.

In this case, when the power cord is drawn out of the cord reel only by a required length, it is prevented from becoming entangled.

The cord reel may be worn on the body of the user via a holder, and the holder may have a mechanism for allowing a cord-dispensing hole of the cord reel to freely point upward, downward, rightward, and leftward.

Since the cord-dispensing hole of the cord reel is thereby controlled so as to constantly point in the extending direction of the power cord (toward a socket), the power cord can be smoothly drawn out of the cord reel.

The controller may have a power cord alarm that sounds an alarm when it is determined that only a short length of power cord remains in the cord reel.

In this case, it is possible to avoid a dangerous operation, in which for example, the power cord is forcibly disconnected from a socket due to a great pulling force applied to a plug because only a short length of power cord remains in the cord reel.

A wearable muscular-force supplementing device according to a further aspect of the present invention includes an artificial muscular-force generator that applies supplementary muscular force for bending to a joint of a user, and a controller that controls the driving of the artificial muscular-force generator, wherein the artificial muscular-force generator has a flexible mounting portion shaped like a cylinder so as to wrap the joint of the user in close contact therewith, and a fluid-pressure type actuator formed integrally with the outer periphery of the mounting portion so as to apply supplementary muscular force to the joint while bending the mounting portion.

In this case, since no member protrudes from the mounting portion, the user can easily wear clothing with the device worn on the body.

The controller may have a heating device that heats fluid serving as working fluid for the actuator to a predetermined temperature.

In this case, when the fluid heated by the heating device flows into the actuator, the temperature of the mounting portion formed integrally with the actuator rises.

The mounting portion may be provided with a muscular force detector that measures muscular force based on pressing force temporarily applied to the skin of the user, and the controller may control supplementary muscular force generated by the actuator based on muscular force information obtained from the muscular force detector. The muscular force detector may include a driving motor, a transmission mechanism that transmits rotating force of the driving motor as linear motion to a pushrod, and a torque measuring instrument that measures the torque value of the driving motor when the skin is pushed by the pushrod and outputting the torque value as the pressing force to the controller.

Since this eliminates the necessity of placing the device into contact with the skin, as in a myoelectric sensor or the like, it is possible to reduce the time for measuring the muscular force and to prevent inflammation of the skin.

The actuator may include an inner actuator placed on the inner side of the joint, extending in the longitudinal direction of the outer periphery of the mounting portion, and having a pressure chamber made of an elastic material, and an outer actuator placed on the outer side of the joint, extending in the longitudinal direction of the outer periphery of the mounting portion, and having a pressure chamber made of an elastic material. The inner and outer actuators may each have a plurality of convex members fixed on the outer periphery of the mounting portion with a predetermined space therebetween in the longitudinal direction, and a plurality of elastic members placed in the spaces between the convex members. Each of the elastic members may be expanded and contracted in response to the inflow and outflow of fluid into and from the pressure chamber formed therein, and each of the convex members may be pressed by expansion of the elastic member so as to apply bending force to the mounting portion.

In this case, when the fluid flows into the pressure chambers of the elastic members of the inner actuator, bending force acts on the mounting portion and supplementary muscular force is applied so as to bend the joint of the user. When the fluid flows into the pressure chambers of the elastic members of the outer actuator, bending force to the mounting portion is released and supplementary muscular force can be applied so as to straighten the joint of the user.

The controller may exert control so as to transfer fluid between the pressure chambers of the elastic members constituting the inner actuator and the pressure chambers of the elastic members constituting the outer actuator.

In this case, the pressure chambers in the outer actuator also serve as reservoirs when putting fluid into the pressure chambers of the inner actuator, and the pressure chambers in the inner actuator also serve as reservoirs when putting fluid into the pressure chambers of the outer actuator. Therefore, no reservoirs are necessary, or only a reservoir having a small capacity is necessary so as to supplement leakage of a small amount of working fluid. This reduces the amount of working fluid and allows a smaller and lighter device.

The actuator may include an outer actuator placed on the outer side of the joint, extending in the longitudinal direction of the outer periphery of the mounting portion, and having a pressure chamber made of an elastic material, and the outer actuator may be expanded in the longitudinal direction in response to the inflow of the fluid into the pressure chamber so as to apply bending force to the mounting portion, and may be contracted in response to the outflow of the fluid from the pressure chamber so as to release the bending force on the mounting portion. The outer actuator may include a plurality of convex members fixed on the outer periphery of the mounting portion with a predetermined space therebetween in the longitudinal direction, and a plurality of elastic members placed in the spaces between the convex members. The elastic members may be expanded in the longitudinal direction in response to the inflow of the fluid in the pressure chamber formed therein so as to press the convex members and to apply bending force to the mounting portion.

In this case, when the outer actuator is expanded so as to apply bending force to the mounting portion, supplementary muscular force is applied to bend the joint of the user. When the outer actuator is contracted so as to release the bending force on the mounting portion, supplementary muscular force is applied to straighten the joint of the user. Since the outer actuator, which is hardened by pressure, is placed on the outer side of the joint, it does not hinder bending of the arm of the user and does not reduce the range of movement of the arm.

The controller may have a generated-force stabilizer that inhibits the force generated by the artificial muscular-force generator from being reduced due to breakage.

In this case, even when the artificial muscular-force generator breaks while the user is carrying something heavy, the generated-force stabilizer prevents the force generated by the artificial muscular-force generator from being suddenly reduced. Therefore, the body of the user will not be injured.

The convex members may function as stopper members for stopping application of supplementary muscular force by contacting with one another before excessive supplementary muscular force is applied to the joint of the user.

This makes it possible to prevent, by the mechanical structure, the joint from bending excessively.

Furthermore, the fluid may be liquid, and the outer periphery of the mounting portion may be coated with a periphery-coating member having a liquid absorbing function.

DETAILED DESCRIPTION OF PREFERRED EMBODIMENTS

Embodiments of a wearable muscular-force supplementing device of the present invention will be described below with reference to the drawings.

Figure 1:
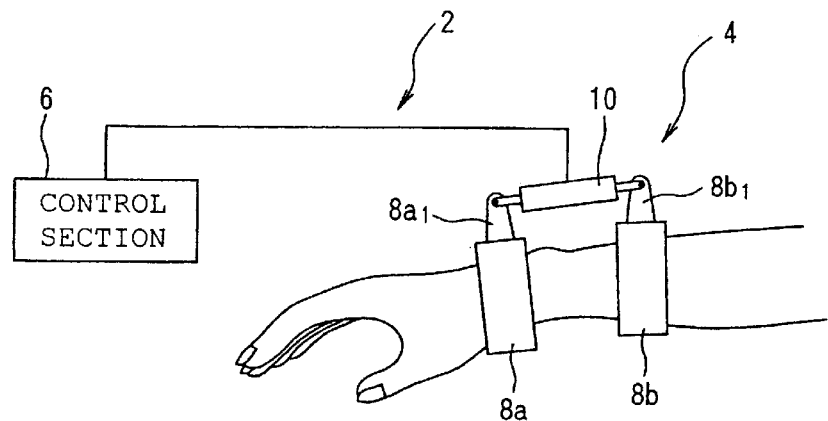
FIG. 1 is a view of a wearable muscular-force supplementing device according to a first embodiment of the present invention.

FIG. 1 shows a muscular-force supplementing device 2 of a first embodiment that applies supplementary muscular force to a wrist joint of a user, which includes an artificial muscular-force generating section 4 and a control section 6 that controls the driving of the artificial muscular-force generating section 4.

The artificial muscular-force generating section 4 includes a pair of mounting portions 8a an 8b to be worn at two positions on both sides of a wrist joint of the user, and an actuator 10 hinged on connecting portions 8a1 and 8b1 of the mounting portions 8a and 8b.

Figure 2:
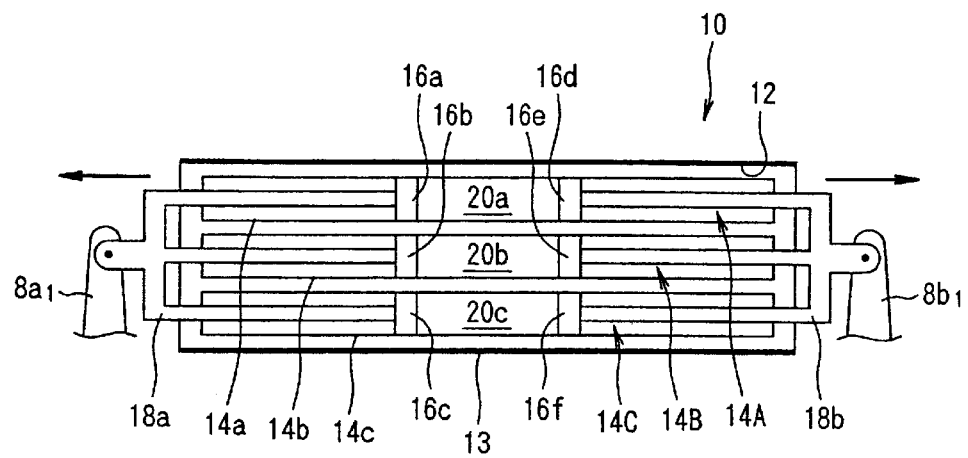
FIG. 2 is a view showing the structure of an actuator constituting an artificial muscular-force generator in the wearable muscular-force supplementing device of the first embodiment.

The actuator 10 is a device having therein a plurality of hydraulic cylinders 14A, 14B, and 14C to be operated in a dual-stroke manner. As shown in FIG. 2, a plurality of cylinders 14a, 14b, and 14c are arranged in parallel in a cylindrical actuator body 12, and pistons 16a to 16f connected to the leading ends of a pair of comb-shaped piston rods 18a and 18b are slidably placed in the cylinders 14a, 14b, and 14c. When hydraulic oil serving as the fluid is supplied to pressure chambers 20a, 20b, and 20c, the piston rods 18a and 18b are extended, and linear actuator force is transmitted to the connecting portions 8a1 and 8b1 of the mounting portions 8a and 8b, thereby transmitting bending force to the joint of the user.

The outer periphery of the actuator 10 is coated with a coating material 13, such as a high polymer, which is able to absorb liquid in order to prevent the hydraulic oil from leaking to the user side.

Figure 3:
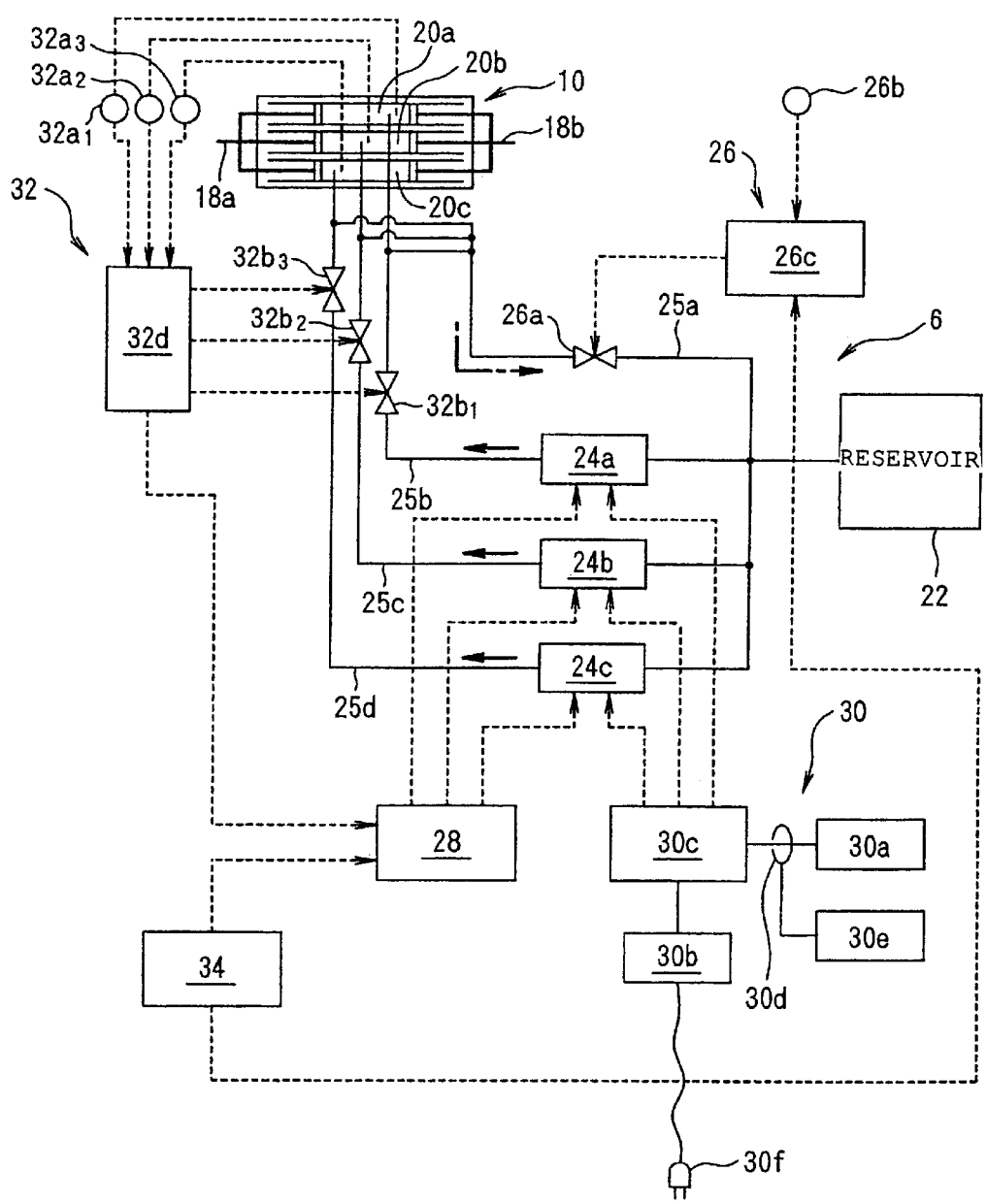
FIG. 3 is a block diagram showing the details of a control section in the wearable muscular-force supplementing device of the first embodiment.

The control section 6 includes, as shown in FIG. 3, a reservoir 22 that stores hydraulic oil to be used in this device, a plurality of hydraulic-oil feeders 24a, 24b, and 24c that independently supply the hydraulic oil in the reservoir 22 to the pressure chambers 20a, 20b, and 20c of the actuator 10, an artificial muscular-force releasing section 26 that releases the force from the artificial muscular-force generating section 4 in the case of an emergency, a feeding-drive control device 28 that controls the driving of the hydraulic-oil feeders 24a, 24b, and 24c, a power supply section 30 that supplies power to the hydraulic-oil feeders 24a, 24b, and 24c, and a generated-force stabilizing section 32 that prevents force generated by the actuator from being decreased suddenly.

The hydraulic-oil feeders 24a, 24b, and 24c are electrically driven and exert control so as to supply the hydraulic oil received from the reservoir 22 to the pressure chambers 20a, 20b, and 20c after increasing the pressure thereof to a predetermined pressure and to return the hydraulic oil.

The artificial muscular-force releasing section 26 includes a control valve 26a interposed in an oil path 25a communicating with the pressure chambers 20a, 20b, and 20c of the actuator 10 and with the reservoir 22 while detouring around the hydraulic-oil feeders 24a, 24b, and 24c, an acceleration sensor 26b that detects the attitude of the user, and an opening control section 26c that outputs a signal for opening to the control valve 26a according to detected information obtained from the acceleration sensor 26b.

The feeding-drive control device 28 controls the operations of the hydraulic-oil feeders 24a, 24b, and 24c. This device is able to activate and deactivate the hydraulic-oil feeders 24a, 24b, and 24c through the operation of switches (not shown) and by voice input.

Specifically, a voice input device 34 is connected to the feeding-drive control device 28, and operation of the feeding-drive control device 28 is controlled in response to signals input from the voice input device 34. For example, when the user says "Start", the hydraulic-oil feeders 24a, 24b, and 24c are activated under control of the feeding-drive control device 28. When the user says "Stop", the hydraulic-oil feeders 24a, 24b, and 24c are deactivated. The voice input device 34 is also connected to the opening control section 26c so that the opening of the control valve 26a can be controlled by voice. For example, when the user says "Danger", the opening control section 26c outputs a signal to open the control valve 26a, so that the control valve 26a is opened.

The power supply section 30 includes two power sources, an external power source serving as a main power source and a storage battery 30a serving as an auxiliary power source. A power circuit 30b of the external power source and the storage battery 30a are connected to a power switching device 30c. When power supply from the power circuit 30b is stopped, the power switching device 30c performs switching so as to supply power from the storage battery 30a for a predetermined period. A current sensor 30d is interposed between the storage battery 30a and the power switching device 30c. When the current sensor 30d detects that the storage battery 30a is being used, an alarm device 30e sounds the alarm.

The generated-force stabilizing section 32 includes pressure sensors 32a1, 32a2, and 32a3 that detect the pressures in the pressure chambers 20a, 20b, and 20c of the actuator 10, control valves 32b1, 32b2, and 32b3 interposed in oil paths 25b, 25c, and 25d that supply hydraulic oil from the hydraulic-oil feeders 24a, 24b, and 24c to the pressure chambers 20a, 20b, and 20c, and a generated-force stabilization control section 32d that obtains pressure information from the pressure sensors 32a1, 32a2, and 32a3, and closing a control valve corresponding to a given pressure chamber in which the pressure is lower than the standard pressure (for example, the control valve 32b1 in the case of the pressure chamber 20a).

A manner of using the muscular-force supplementing device 2 with the above configuration will be described below briefly.

First, a power cord 30*f* of the power supply section 30 is placed into contact with a socket (not shown). Then, as shown in FIG. 1, the mounting portions 8*a* and 8*b* are put on the hand and arm sides of the user. Subsequently, the hydraulic-oil feeders 24*a*, 24*b*, and 24*c* are activated by operating the switches in the feeding-drive control device 28.

The hydraulic-oil feeders 24*a*, 24*b*, and 24*c* increase the pressure of the hydraulic oil received from the reservoir 22 to a predetermined pressure, and supply the hydraulic oil to the pressure chambers 20*a*, 20*b*, and 20*c* of the actuator 10, respectively. When the hydraulic oil serving as the fluid is supplied to the pressure chambers 20*a*, 20*b*, and 20*c*, the artificial muscular-force generating section 4 is extended in response to the supply of the hydraulic oil to the actuator 10, linear actuator force acts on the connecting portions 8*a*1 and 8*a*2 of the mounting portions 8*a* and 8*b*, and bending force (supplementary muscular force) is thereby transmitted to the joint of the user. After a predetermined time, the hydraulic-oil feeders 24*a*, 24*b*, and 24*c* return the hydraulic oil in the pressure chambers 20*a*, 20*b*, and 20*c* to the reservoir 22 so as to discontinue the transmission of the supplementary muscular force to the joint of the user.

If the user, who is wearing and walking with the muscular-force supplementing device 2, is going to fall down, the acceleration sensor 26*b* of the artificial muscular-force releasing section 26 detects a specific acceleration value in the state in which the user is going to fall down. In this case, the opening control section 26*c* outputs a signal for opening to the control valve 26*a* based on the specific acceleration value input from the acceleration sensor 26*b*, thereby placing the control valve 26*a* into an open state. When the control valve 26*a* is placed in the open state, the hydraulic oil in the pressure chambers 20*a*, 20*b*, and 20*c* is returned to the reservoir 22 via the oil path 25*a*, and the actuator force of the artificial muscular-force generating section 4 is decreased to zero. In this way, when the user is going to fall down, the artificial muscular-force releasing section 26 releases the muscular-force supplementing device 2 from restraint.

In the muscular-force supplementing device 2, the artificial muscular-force generating section 4 can be controlled so as to start and stop generation of supplementary muscular force and the artificial muscular-force releasing section 26 is operated to release the joint from restraint, not only by operating the switches (the switches of the feeding-drive control device 28), but also by inputting voice to the voice input device 34. This makes it possible to easily respond to a demand for an emergency stop during use.

When power supply to the external power source is stopped during operation of the muscular-force supplementing device 2, the power switching device 30*c* performs switching so that power is supplied from the storage battery 30*a*. In this case, the alarm device 30*e* sounds an alarm so as to inform the user that the power is being supplied from the storage battery 30*a*.

When the power cord 30*f* is disconnected from the socket, the power switching device 30*c* also performs switching so as to supply power from the storage battery 30*a*, and the alarm device 30*e* sounds an alarm.

In a case in which trouble, such as oil leakage, occurs in any of the hydraulic cylinders constituting the actuator 10, for example, when the actuator force of the hydraulic cylinder 14A is reduced, the generated-force stabilizing section 32 exerts the following control. Specifically, the generated-force stabilization control section 32*d* ascertains, based on information from the pressure sensor 32*a*1, that the pressure in the pressure chamber 20*a* has fallen, and outputs a closing signal to the control valve 32*b*1 corresponding to the pressure chamber 20*a*. The faulty hydraulic cylinder 14A is thereby separated so as to prevent the force from being lost due to leakage of all the oil. The other hydraulic cylinders 14B and 14C generate the minimum required actuator force.

Therefore, in a case in which the user of the muscular-force supplementing device 2 of this embodiment is in a dangerous attitude, for example, in a case in which the user is going to fall down, the muscular-force supplementing device 2 is released by reducing the actuator force of the artificial muscular-force generating section 4 to zero under control of the artificial muscular-force releasing section 26. This allows the user to freely move the joint and to quickly assume a recovery attitude.

By inputting voice to the voice input device 34, the operation of the muscular-force supplementing device 2 can be started and stopped, and the artificial muscular-force releasing section 26 can be operated to release the joint. Therefore, the muscular-force supplementing device 2 can be used safely.

Since the power supply section 30 that supplies power to the hydraulic-oil feeders 24*a*, 24*b*, and 24*c* can obtain power from the storage battery 30*a* when the power supply from the external power source is stopped, it is possible to avoid dangers, such as a sudden loss of supplementary muscular force, and to apply supplementary muscular force until the user assumes a safe attitude.

Since the alarm device 30*e* sounds an alarm so as to inform the user that the power is being supplied from the storage battery 30*a*, it is possible to immediately ascertain the cause, for example, the disconnection of the power cord 30*f* from the socket.

Even when any of the hydraulic cylinders of the actuator 10 is faulty, the generated-force stabilizing section 32 exerts control so as to generate the minimum required actuator force. Therefore, it is possible to avoid dangers, for example, damage to the joint due to a sudden loss of supplementary muscular force while the user is carrying something heavy.

Since the actuator 10 of this embodiment is constituted by a plurality of hydraulic cylinders 14A, 14B, and 14C to be operated in a dual-stroke manner, it allows linear actuator force to reliably act on the connecting portions 8*a*1 and 8*b*1 of the mounting portions 8*a* and 8*b*, so that supplementary muscular force appropriate for bending can be transmitted to the joint of the user.

Figure 4:
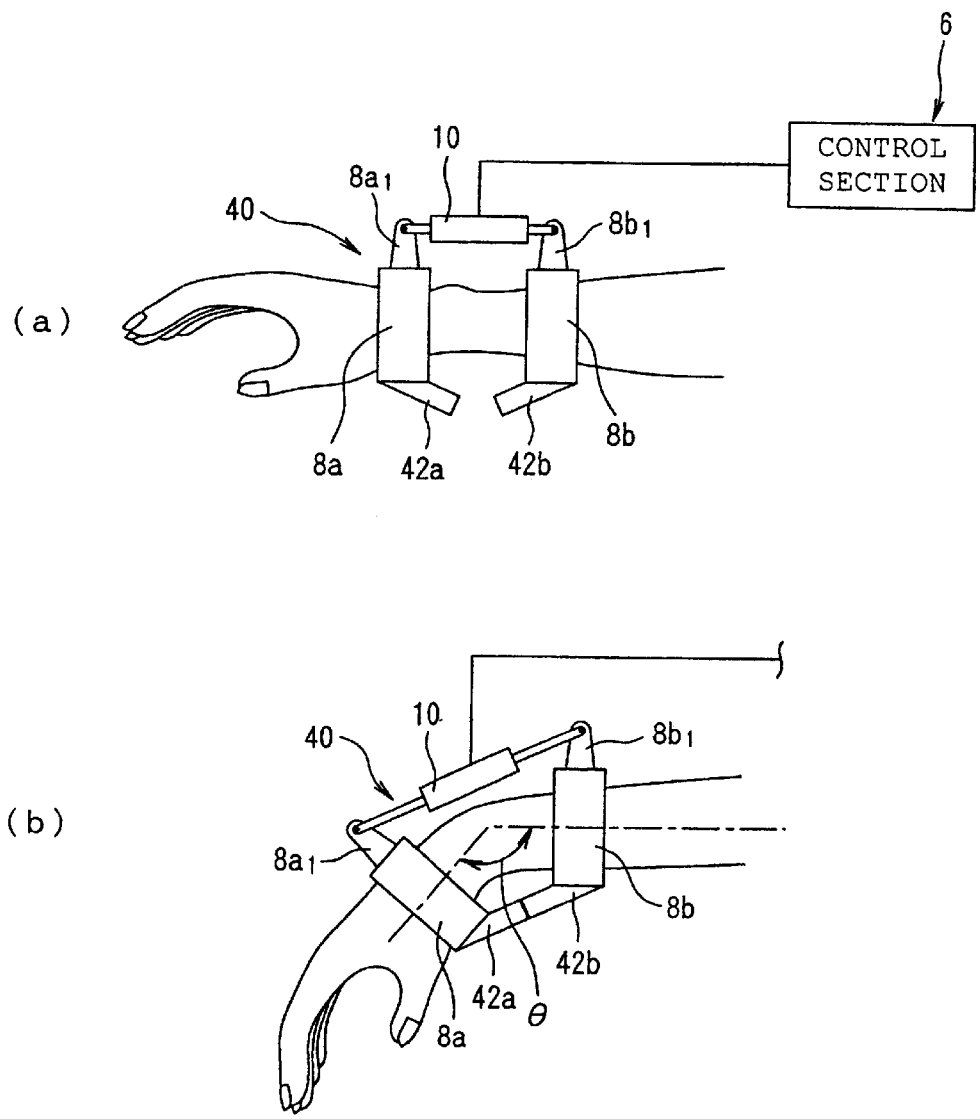
FIGS. 4(*a*) and 4(*b*) are views of a wearable muscular-force supplementing device according to a second embodiment.

FIGS. 4(*a*) and 4(*b*) show a muscular-force supplementing device 40 of a second embodiment which has a structure different from that of the first embodiment shown in FIGS. 1 to 3. The same components as those in the first embodiment are denoted by the same numerals, and descriptions thereof are omitted.

In this embodiment, as shown in FIG. 4(*a*), a pair of mounting portions 8*a* and 8*b* are provided with a pair of stopper members 42*a* and 42*b* made of a hard material and placed opposed to each other. The stopper members 42*a* and 42*b* contact at the maximum bending angle (allowable bending angle) θ which does not have any influence on a joint of the user, as shown in FIG. 4(*b*), thereby inhibiting the joint from being bent at an angle greater than the allowable bending angle θ. While the allowable bending angle θ of the joint varies among users, the distance between the stopper members 42*a* and 42*b* is adjustable.

Since the contacted stopper members 42*a* and 42*b* thereby prevent the joint from bending excessively, it is possible to provide a muscular-force supplementing device with greater safety.

Figure 5:
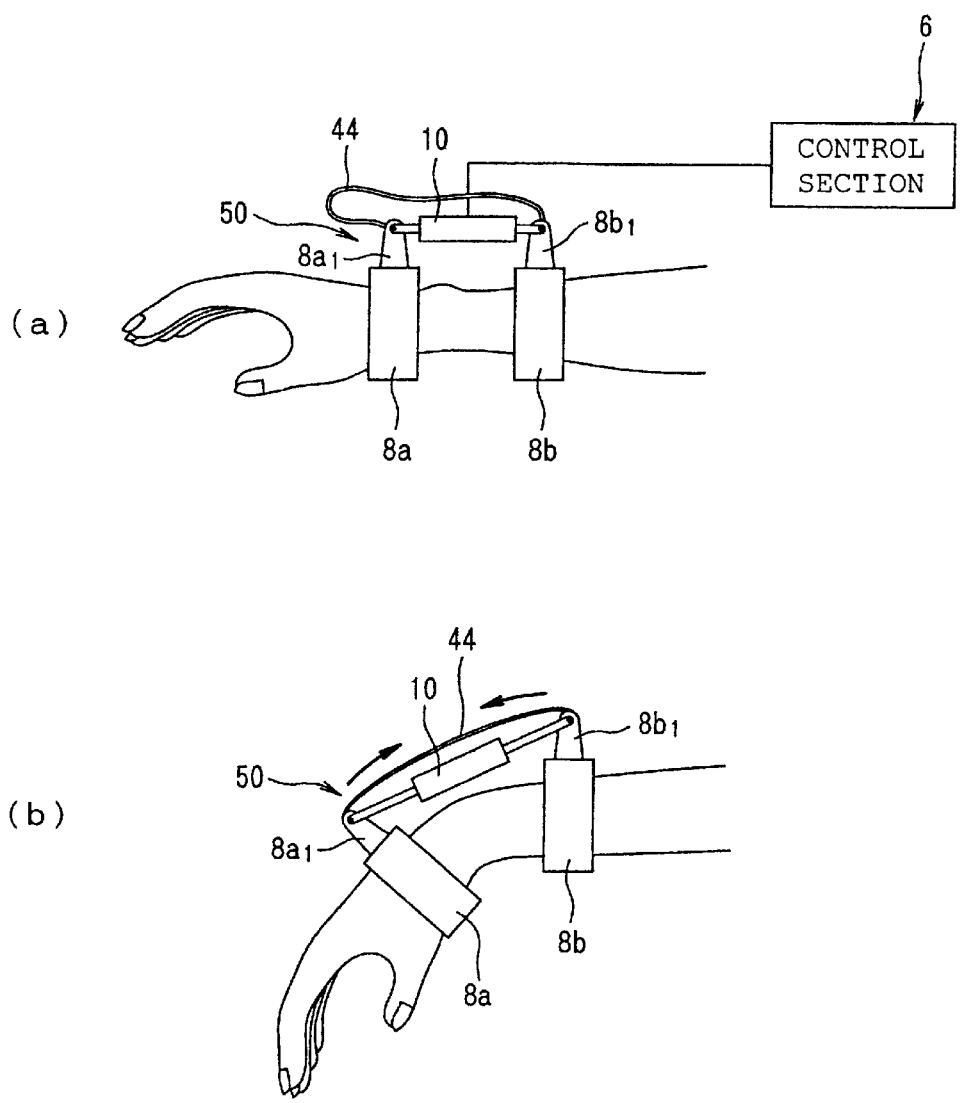
FIGS. 5(*a*) and 5(*b*) are views of a wearable muscular-force supplementing device according to a third embodiment.

FIGS. 5(*a*) and 5(*b*) show a muscular-force supplementing device 50 according to a third embodiment. In this embodiment, as shown in FIG. 5(*a*), an elastic belt 44 is connected between connecting portions 8*a*1 and 8*a*2 of mounting portions 8*a* and 8*b*. At the allowable bending angle θ of a user, the elastic belt 44 inhibits, by its own tension, a joint from being bent at an angle greater than the allowable bending angle θ, as shown in FIG. 5(*b*). When using the elastic belt 44, the length thereof is adjusted in accordance with the allowable bending angle θ of the joint of the user.

Since this prevents the joint from bending excessively, in a manner similar to that in the second embodiment, it is possible to provide a muscular-force supplementing device with greater safety.

Figure 6:
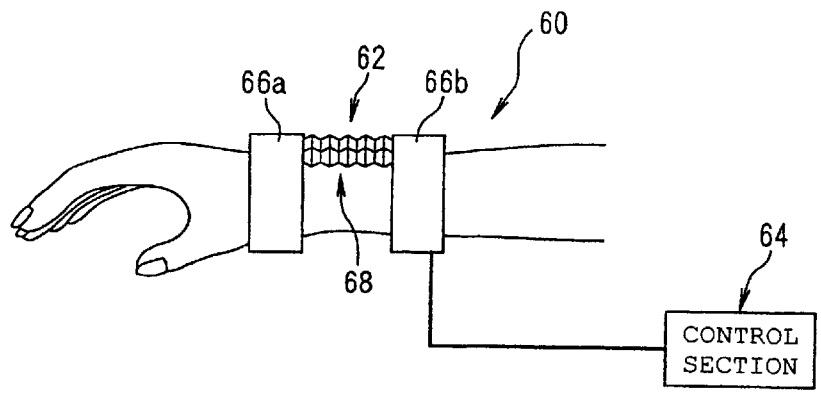
FIG. 6 is a view of a wearable muscular-force supplementing device according to a fourth embodiment.

FIG. 6 shows a muscular-force supplementing device 60 of a fourth embodiment. This device 60 includes an artificial muscular-force generating section 62, and a control section 64 that controls the driving of the artificial muscular-force generating section 62.

The artificial muscular-force generating section 62 includes first and second mounting portions 66*a* and 66*b* worn at two positions on both sides of a wrist joint of the user, and a hydraulic actuator 68 detachably connected between the first and second mounting portions 66*a* and 66*b*.

Figure 7:
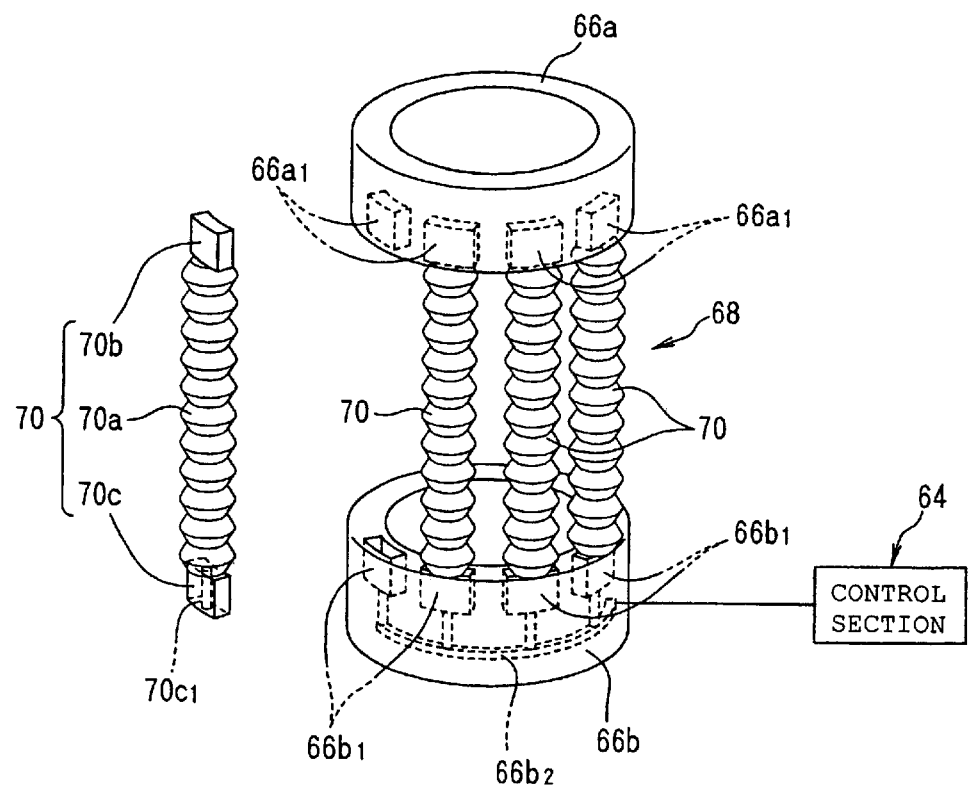
FIG. 7 is a view of an artificial muscular-force generator in the wearable muscular-force supplementing device of the fourth embodiment.

FIG. 7 concretely shows the structure of the artificial muscular-force generating section 62. The first mounting portion 66*a* is provided with concave detachably connecting portions 66*a*1 which are arranged at predetermined intervals in the circumferential direction on the side opposing the second mounting portion 66*b*. The second mounting portion 66*b* is also provided with concave detachably connecting portions 66*b*1 which are arranged at predetermined intervals in the circumferential direction on the side opposing the first mounting portion 66*a*.

The actuator 68 includes a plurality of actuator divisions 70 placed in parallel, as shown in FIG. 7. Each of the actuator divisions 70 includes an elongated expandable portion 70*a* having a pressure chamber therein so as to expand in the longitudinal direction and to thereby generate a predetermined amount of actuator force, and connecting portions 70*b* and 70*c* fixed to both ends of the expandable portion 70*a*.

One of the connecting portions 70*b* is fitted in the detachably connecting portion 66*a*1 of the first mounting portion 66*a*, and the other connecting portion 70*c* is fitted in the detachably connecting portion 66*b*1 of the second mounting portion 66*b*, whereby a plurality of actuator divisions 70 are detachably connected between the first and second mounting portions 66*a* and 66*b*.

The other connecting portion 70*c* of each of the actuator divisions 70 has an oil path 70*c*1 communicating with the pressure chamber. One end of an oil path 66*b*2 formed inside the second mounting portion 66*b* is opened in the detachably connecting portions 66*b*1 of the second mounting portion 66*b*. The oil path 66*b*2 is connected to a feed and feedback control section 74 of the control section 64, which will be described later. When the other connecting portions 70*c* of the actuator divisions 70 are fitted in the detachably connecting portions 66*b*1, the oil path 70*c*1 and the oil path 66*b*2 are caused to communicate with each other.

It is assumed that the detachably connecting portion 66*b*1 of the second mounting portion 66*b*, to which the actuator division 70 is not connected, is disconnected from the oil path 66*b*2 by a blocking device that is not shown.

When hydraulic oil is supplied from the control section 64 to the artificial muscular-force generating section 62, it flows into the pressure chambers in the actuator divisions 70 connected between the first and second mounting portions 66*a* and 66*b*, and the expandable portions 70*a* are thereby expanded. Then, substantially linear actuator force is transmitted to the mounting portions 66*a* and 66*b*, and bending force is transmitted to the joint of the user.

Figure 9:
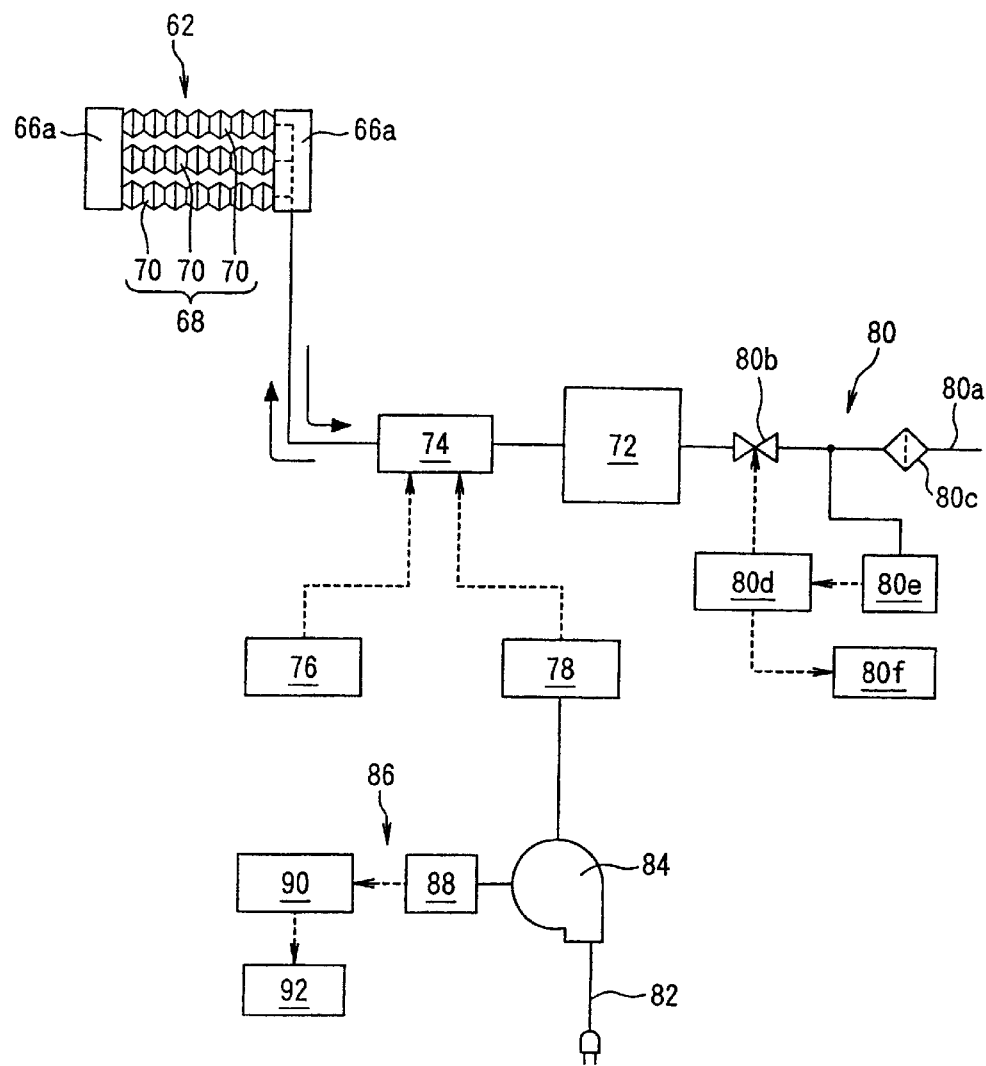
FIG. 9 is a block diagram showing the details of a control section in the wearable muscular-force supplementing device of the fourth embodiment.

As shown in FIG. 9, the control section 64 includes a reservoir 72 that stores hydraulic oil, a feed and feedback control section 74 that controls feeding and feedback of hydraulic oil to and from the actuator divisions 70 constituting the artificial muscular-force generating section 62, a driving control device 76 that controls the driving of the feed and feedback control section 74, a power supply section 78 that supplies external power to the feed and feedback control section 74, a hydraulic oil supply and discharge section 80 that supplies hydraulic oil to the reservoir 72 or discharging hydraulic oil in the reservoir 72, a cord reel 84 that winds up a power cord 82 extending from the power supply section 78, and a power cord alarm section 86 that sounds an alarm when the length of the power cord 82 remaining in the cord reel 84 is short.

The feed and feedback control section 74 is electrically driven and exerts control so as to feed hydraulic oil, which is received from the reservoir 72, to the actuator divisions 70 and to feed back hydraulic oil in the pressure chambers of the actuator divisions 70 to the reservoir 72.

The hydraulic oil supply and discharge section 80 includes a supply and discharge tube 80*a* connected to the reservoir 72 at one end, an on-off valve 80*b* interposed in the supply and discharge tube 80*a*, an oil filter 80*c* placed on an open-end side of the supply and discharge tube 80*a*, and a valve control section 80*d* that controls opening and closing of the on-off valve 80*b*. A leakage detector 80*e* that detects leakage of hydraulic oil is connected to a portion of the supply and discharge tube 80*a* between the on-off valve 80*b* and the oil filter 80*c*. An alarm device 80*f* is connected to the valve control section 80*d*. When the leakage detector 80*e* detects that hydraulic oil is leaking when the supply and discharge tube 80*a* is insulated from outside air by closing the on-off valve 80*b* under control of the valve control section 80*d*, the valve control section 80*d* outputs a signal to the alarm device 80*f* so that the alarm device 80*f* sounds an alarm. The supply and discharge tube 80*a*, the on-off valve 80*b*, the valve control section 80*d*, the leakage detector 80*e*, and the alarm device 80*f* correspond to the fluid discharge control section of the present invention. The supply and discharge tube 80*a*, the on-off valve 80*b*, the valve control section 80*d*, and the oil filter 80*c* correspond to the fluid supply control section of the present invention.

On the other hand, the cord reel 84 is worn on the body of the user via a holder 102 that will be described later (see FIG. 11). The user winds up the power cord 82 by a predetermined length. The power cord alarm section 86 monitors the state of the power cord 82 drawn from the cord reel 84.

As shown in FIG. 9, the power cord alarm section 86 includes a cord length detector 88, a cord length determining section 90 that determines the length of the power cord 82 drawn from the cord reel 84 based on the detection result of the cord length detector 88, and an alarm device 92 for sounding an alarm in response to a signal output from the cord length determining section 90 when the length of the power cord 82 remaining in the cord reel 84 is short.

Figure 10:
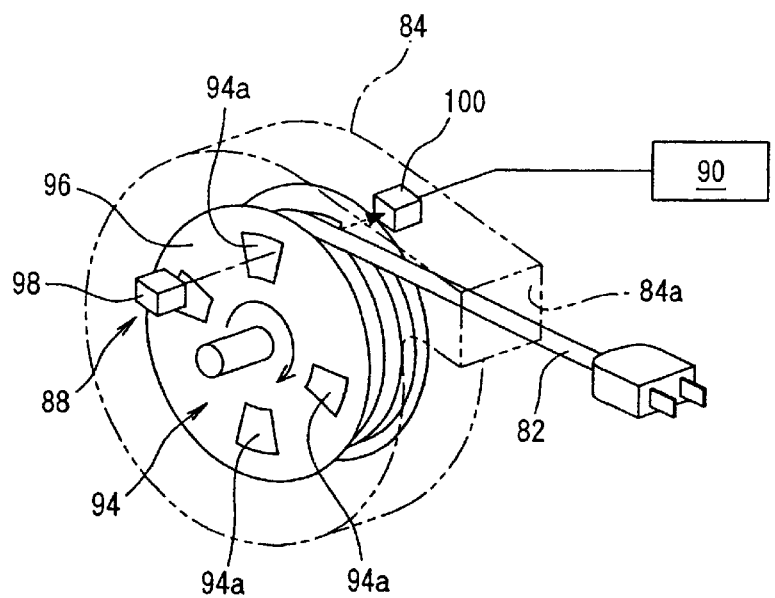
FIG. 10 is a view of a cord reel constituting the wearable muscular-force supplementing device of the fourth embodiment.

The cord length detector 88 may have a structure shown in FIG. 10 in which a plurality of slits 94*a* are formed on the outer peripheries of rotating disks 96 of a drum 94 built in the cord reel 84 and a light-emitting element 98 and a photodiode 100 are arranged opposed to the positions of the slits 94*a*. In this structure, light emitted from the light-emitting element 98 is received by the photodiode 100 via the slits 94*a* and the light traveling toward the photodiode 100 is blocked at the positions where no slits 94*a* are formed. The photodiode 100 outputs, to the cord length determining section 90, a signal when the drum 94 is rotated by a predetermined angle in order to draw the power cord 82. The cord length determining section 90 determines the length of the power cord 82 drawn from the drum 94 based on the signal obtained from the photodiode 100. While the cord reel 84 is worn on the body of the user via the holder 102, as shown in FIG. 11, the holder 102 has a gyro mechanism that rotates the entire cord reel 84 so that a cord-dispensing hole 84*a* of the cord reel 84 freely points upward and downward or rightward and leftward.

A manner of using the muscular-force supplementing device 60 with the above configuration will be briefly described below with reference to FIGS. 6 to 11.

First, a predetermined amount of hydraulic oil is stored in the reservoir 72 through the supply and discharge tube 80*a*. In this case, since the oil filter 80*c* is interposed in the supply and discharge tube 80*a*, it removes impurities, such as dust, mixed in the hydraulic oil.

Subsequently, as shown in FIG. 7, a predetermined number of actuator divisions 70 are connected to the detachably connecting portions 66*a*1 and 66*b*2 of the first and second mounting portions 66*a* and 66*b* so as to generate actuator force in accordance with the power of muscular force that the user desires.

Then, the mounting portions 66*a* and 66*b* are put on the hand and arm sides of the user, as shown in FIG. 6.

Figure 11:
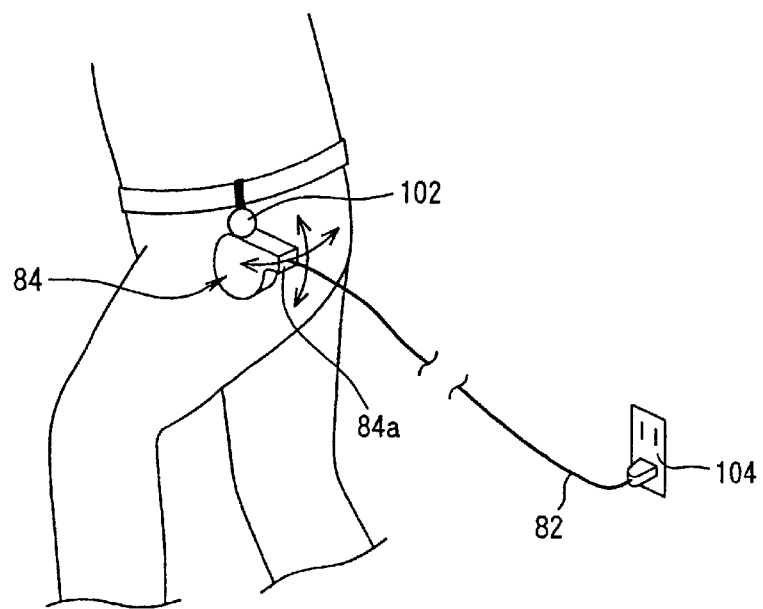
FIG. 11 is a view showing a state in which the cord reel as a component of the fourth embodiment is worn on the body of a user.

Subsequently, the power cord 82 is drawn from the cord reel 84 by a required length, and a plug of the power cord 82 is put into a socket 104, as shown in FIG. 11. When the power cord 82 is thus drawn out of the cord reel 84 by the required length, it can be prevented from becoming entangled.

Then, the feed and feedback control section 74 is operated so as to generate supplementary muscular force in the artificial muscular-force generating section 62.

Figure 8:
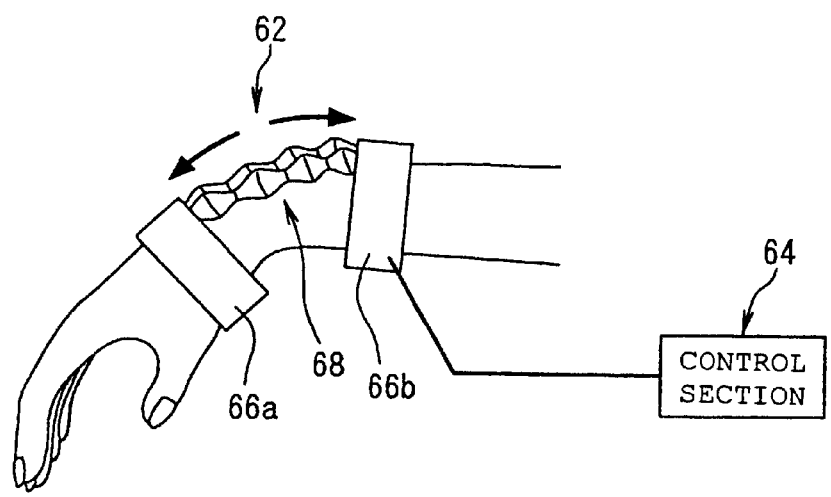
FIG. 8 is a view showing a state in which the artificial muscular-force generator of the fourth embodiment is generating supplementary muscular force.

Specifically, the feed and feedback control section 74 increases the pressure of the hydraulic oil received from the reservoir 72 to a predetermined pressure and supplies the hydraulic oil to the pressure chambers of the actuator divisions 70. When the hydraulic oil is supplied to the pressure chambers, the actuator divisions 70 are expanded so as to apply linear actuator force to the first and second mounting portions 66*a* and 66*b*, as shown in FIG. 8, and bending force (supplementary muscular force) is transmitted to the joint of the user. After a predetermined time, the feed and feedback control section 74 returns the hydraulic oil in the pressure chambers of the actuator divisions 70 to the reservoir 72, thereby discontinuing transmission of the supplementary muscular force to the joint of the user.

The user wears the cord reel 84 on the body via the holder 102, as shown in FIG. 11. Since the gyro mechanism built in the holder 102 exerts control so that the cord-dispensing hole 84*a* of the cord reel 84 is constantly oriented in the extending direction of the power cord 82 (toward the socket 104), the power cord 82 can be smoothly drawn out of the cord reel 84.

In a case in which the length of the power cord 82 remaining in the cord reel 84 is short, the cord length determining section 90 of the power cord alarm section 86 outputs a signal to the alarm device 92 based on information about the length of the power cord 82 obtained from the cord length detector 88. The alarm device 92, to which the signal is input from the cord length determining section 90, sounds an alarm, whereby the user can ascertain that the length of the power cord 82 presently remaining in the cord reel 84 is short.

In a case in which hydraulic oil is leaking from the supply and discharge tube 80*a*, for example, due to trouble of the on-off valve 80*b* while supplementary muscular force is being generated in the artificial muscular-force generating section 62, the valve control section 80*d* outputs a signal to the alarm device 80*f* based on a leakage information signal from the leakage detector 80*e*. The alarm device 80*f*, to which the signal is input from the valve control section 80*d*, sounds an alarm, and this allows the user to ascertain that the hydraulic oil is leaking from the supply and discharge tube 80*a*. When moving the muscular-force supplementing device 60, which is placed in a non-operation state, to another place, the hydraulic oil in the reservoir 72 is discharged to the outside through the supply and discharge tube 80*a*. The actuator divisions 70 connected to the detachably connecting portions 66*a*1 and 66*b*2 of the first and second mounting portions 66*a* and 66*b* are also detached. The weight of the entire control section 64, from which the hydraulic oil is discharged, is reduced, and the artificial muscular-force generating section 62, in which the first and second mounting portions 66*a* and 66*b* and the actuator divisions 70 are separated, is made compact.

Therefore, according to the muscular-force supplementing device 60 of this embodiment, since actuator force can be varied only by connecting a predetermined number of actuator divisions 70 to the detachably connecting portions 66*a*1 and 66*b*2 of the first and second mounting portions 66*a* and 66*b*, it is possible to freely set the power of supplementary muscular force as the user desires.

The other connecting portions 70*c* of the actuator divisions 70 have the oil paths 70*c*1 communicating with the pressure chambers of the actuator divisions 70. When the other connecting portions 70*c* of the actuator divisions 70 are fitted, the oil paths 70*c*1 and the oil path 66*b*2 are caused to communicate with each other. Therefore, tubes for supplying hydraulic oil and the like are not exposed outside the device, and the artificial muscular-force generating section 62 can be handled easily.

When storing a predetermined amount of hydraulic oil in the reservoir 72, the oil filter 80 interposed in the supply and discharge tube 80*a* can remove impurities, such as dust, mixed in the hydraulic oil. For this reason, the feed and feedback control section 74 exerts control to feed and feed back hydraulic oil containing no impurities, which can substantially reduce problems due to impurities.

By discharging hydraulic oil in the reservoir 72 by using the supply and discharge tube 80*a*, the device is decreased in weight. By detaching the actuator divisions 70 connected to the detachably connecting portions 66*a*1 and 66*b*2 of the first and second mounting portions 66*a* and 66*b*, the artificial muscular-force generating section 62 can be made compact. This allows the muscular-force supplementing device 60 in a non-operation state to be easily moved to another place. Moreover, the storage space for the device can be reduced.

Since the alarm device 80f of the hydraulic oil supply and discharge section 80 sounds an alarm, it is possible to immediately inform the user that an abnormal condition exists in which hydraulic oil in the reservoir 72 is leaking to the outside.

Since the alarm device 92 of the power cord alarm section 86 sounds an alarm, it is possible to immediately inform the user that the length of the power cord 82 presently remaining in the cord reel 84 is short. This makes it possible to prevent the power cord 82 from being completely pulled out of the socket 104 because the power cord 82 is excessively drawn.

Figure 12:
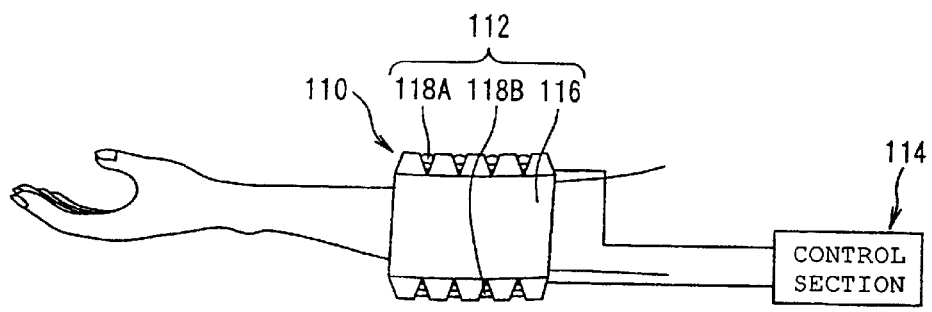
FIG. 12 is a view of a wearable muscular-force supplementing device according to a fifth embodiment of the present invention.

FIG. 12 shows a muscular-force supplementing device 110 according to a fifth embodiment. This device 110 includes an artificial muscular-force generating section 112 and a control section 114 that controls the driving of the artificial muscular-force generating section 112.

The artificial muscular-force generating section 112 includes a mounting portion 116, and an inner actuator 118A and an outer actuator 118B formed integrally with the outer periphery of the mounting portion 116. Herein, "inner" of the inner actuator 118A refers to the interior-angle side of a joint of a user at which the device is worn. In contrast, "outer" of the outer actuator 118B refers to the exterior-angle side of the joint of the user at which the device is worn.

Figure 13:
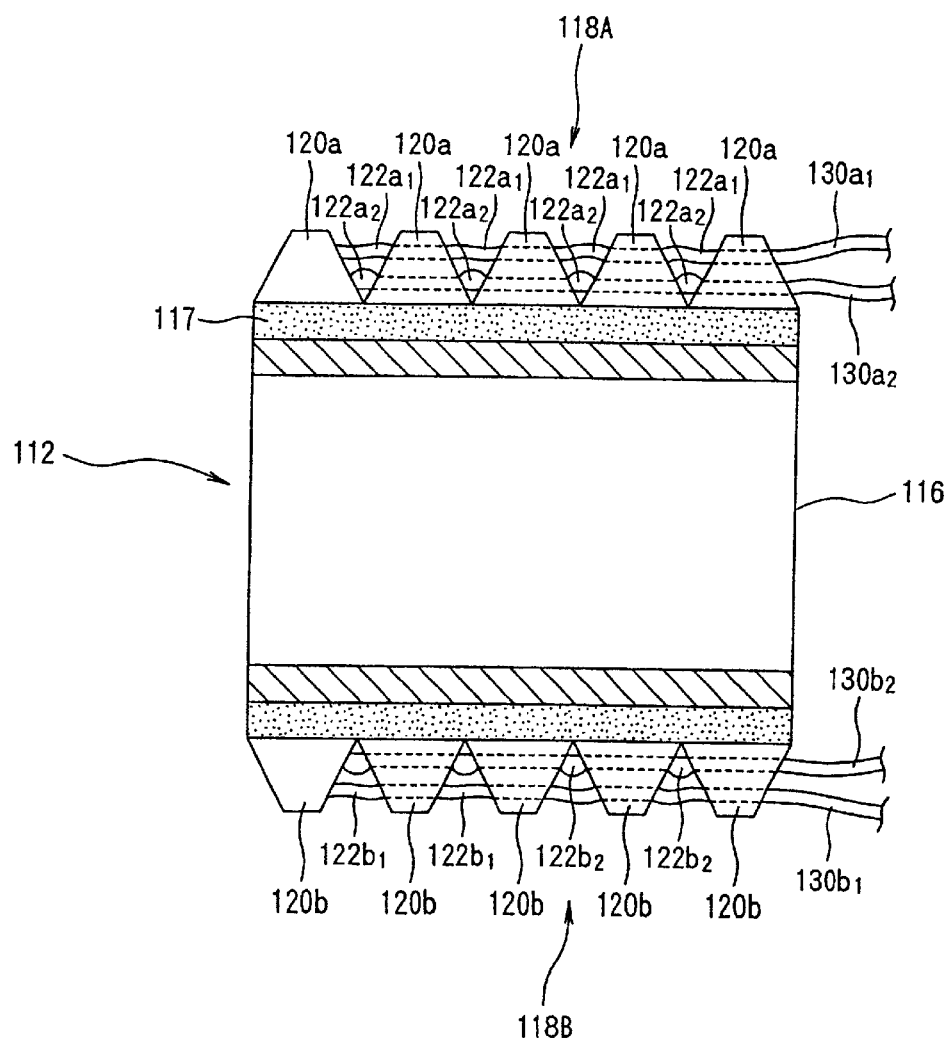
FIG. 13 is a view showing the structure of an actuator constituting an artificial muscular-force generator in the wearable muscular-force supplementing device of the fifth embodiment.

The mounting portion 116 is a flexible member made of leather, a synthetic resin sheet, or the like, and is shaped like a cylinder so as to wrap the joint of the user in close contact therewith. The outer periphery of the mounting portion 116 is coated with a flexible coating material 117 made of a high polymer which is able to absorb liquid, as shown in FIG. 13.

The inner actuator 118A is operated by fluid pressure, and includes a plurality of blocks 120a made of a hard material, which are arranged in the longitudinal direction of the mounting portion 116 with a predetermined space therebetween and are fixed on the coating material 117, and a plurality of elastic members 122a1 and 122a2 placed in the spaces between the blocks 120a. The elastic members 122a1 placed on the outer periphery of the mounting portion 116 have pressure chambers therein, are connected in serial to one another via oil paths formed in the blocks 120a, and are connected to an oil path 130a1 extending to the control section 114 which will be described later. The elastic members 122a2 placed adjacent to the mounting portion 116 are also connected with one another via oil paths formed in the blocks 120a and are connected to an oil path 130a2 extending to the control section 114.

The space and height of the above-described blocks 120a are set so that the adjoining blocks 120a contact to stop application of supplementary muscular force before supplementary muscular force is excessively applied to the joint of the user.

The outer actuator 118B is also operated by fluid pressure, and includes a plurality of blocks 120b arranged in the longitudinal direction of the mounting portion 116 with a predetermined space therebetween and fixed on the coating material 117, and a plurality of elastic members 122b1 and 122b2 placed in the spaces between the blocks 120b. The elastic members 122b1 placed on the outer periphery of the mounting portion 116 have pressure chambers therein, are connected in serial to one another via oil paths formed in the blocks 120b, and are connected to an oil path 130b1 extending to the control section 114. The elastic members 122b2 placed adjacent to the mounting portion 116 are also connected in serial with one another via oil paths formed in the block members 120b and are connected to an oil path 130b2 extending to the control section 114.

Figure 14:
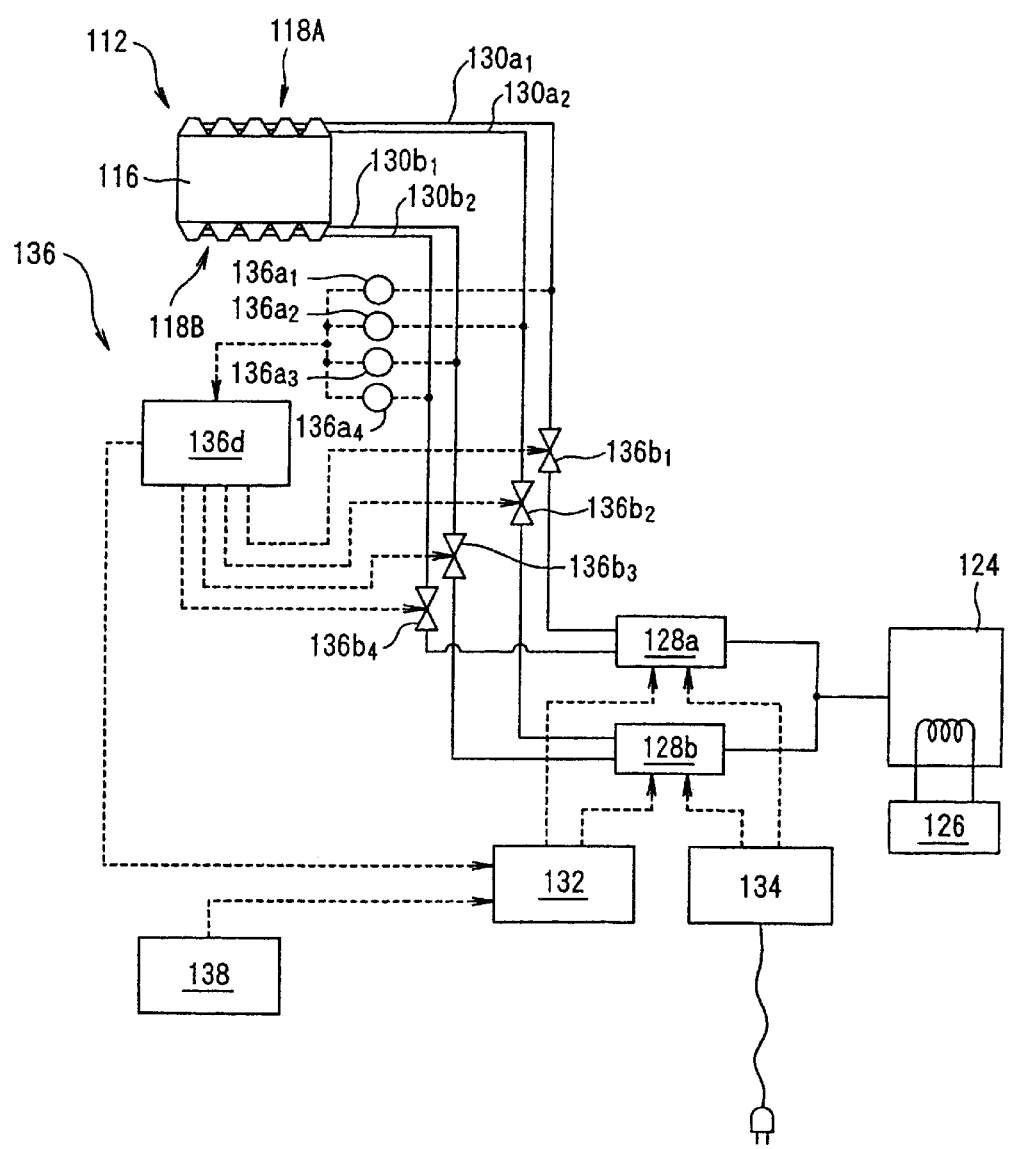
FIG. 14 is a block diagram showing the details of a control section in the wearable muscular-force supplementing device of the fifth embodiment.
Figure 15:
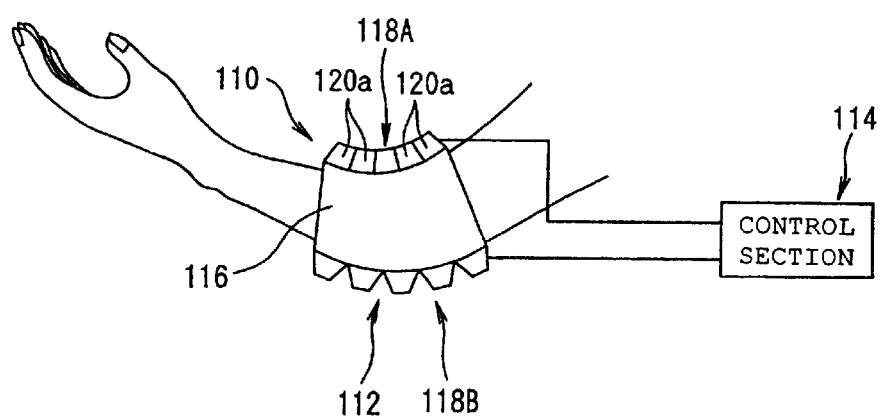
FIG. 15 is a view showing the operation of the wearable muscular-force supplementing device of the fifth embodiment.

As shown in FIG. 14, the control section 114 includes a reservoir 124 that stores hydraulic oil to be used in the device, a heater 126 that heats the hydraulic oil in the reservoir 124 to a predetermined temperature, a plurality of hydraulic-oil feeders 128a and 128b that independently supplies the hydraulic oil in the reservoir 124 to the inner actuator 118A and the outer actuator 118B, a feeding-drive control device 132 that controls the driving of the hydraulic-oil feeders 128a and 128b, a power supply section 134 that supplies power to the hydraulic-oil feeders 128a and 128b, and a generated-force stabilizing section 136 that prevents generated actuator force from being suddenly decreased even when trouble occurs in a portion of the inner and outer actuators 118A and 118B.

After supplying hydraulic oil in the reservoir 124 to the inner actuator 118A and the outer actuator 118B, the hydraulic-oil feeder 128a exchanges hydraulic oil between the pressure chambers of the elastic members 122a1 of the inner actuator 118A and the pressure chambers of the elastic members 122b1 of the outer actuator 118B via the oil paths 130a1 and 130b1. The hydraulic-oil feeder 128b exchanges hydraulic oil between the pressure chambers of the elastic members 122a2 of the inner actuator 118A and the pressure chambers of the elastic members 122b2 of the outer actuator 118B via the oil paths 130a2 and 130b2.

The feeding-drive control device 132 controls the operations of the hydraulic-oil feeders 128a and 128b. Information about the muscular force of the user is input from a muscular-force detector 138 to the device 132.

Figure 16:
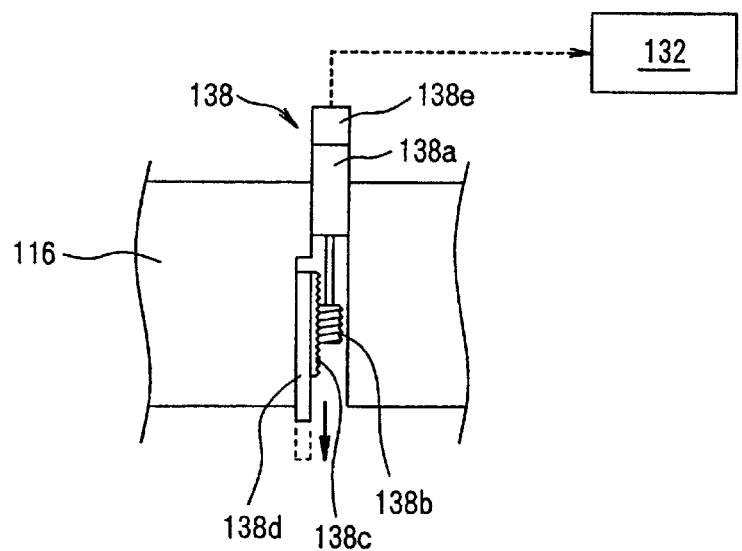
FIG. 16 is a view of a muscular-force detector provided in the wearable muscular-force supplementing device of the fifth embodiment.

The muscular force detector 138 includes, as shown in FIG. 16, a driving motor 138a placed in a through hole extending toward the inner peripheral surface of the mounting portion 116 so that its rotation shaft points inward, a gear 138b fixed to the rotation shaft of the driving motor 138a, a rack 138c meshed with the gear 138b, a pushrod 138d formed integrally with the rack 138c and movably placed in the mounting portion 116, and a torque measuring instrument 138e placed at the top of the driving motor 138a. Rotational motion of the driving motor 138a is converted into linear motion of the pushrod 138d via the gear 138b and the rack 138c, and pressing force is applied from the pushrod 138d to the skin of the user. Since the torque of the driving motor 138a is changed by the pressing force, the torque value is detected by the torque measuring instrument 138e and is output to the feeding-drive control device 132.

Referring again to FIG. 14, the generated-force stabilizing section 136 includes a plurality of pressure sensors 136a1, 136a2, 136a3, and 136a4 that detects the pressures in the oil paths 130a1, 130b1, 130a2, and 130b2, control valves 136b1, 136b2, 136b3, 136b4 interposed in the oil paths 130a1, 130b1, 130a2, and 130b2, and a generated-force generation control section 136d that obtains pressure information from the pressure sensors 136a1, 136a2, 136a3, and 136a4, and closes a control valve corresponding to a pressure chamber of a given elastic member where the pressure is lower than the standard pressure (for example, the control valve 136b1 in the case of the pressure chamber of the elastic member 122a1).

A manner of using the muscular-force supplementing device 110 with the above-described configuration will be briefly described with reference to FIGS. 12 to 15.

First, the mounting portion 116 is put on the arm of the user, as shown in FIG. 12. Subsequently, the muscular-force detector 138 is activated so as to measure the hardness of muscles of the user while temporarily pressing the pushrod 138d against the skin of the user. Muscle information obtained based on the measured value is output to the feeding-drive control device 132. The feeding-drive control device 132 starts operation of the hydraulic-oil feeders 128a and 128b based on the obtained information about the muscle of the user.

The hydraulic-oil feeders 128a and 128b receive heated hydraulic oil from the reservoir 124 and exchange hydraulic oil between the inner actuator 118A and the outer actuator 118B.

In order to transmit bending force (supplementary muscular force) to the joint of the user, control is exerted so as to transfer hydraulic oil in the pressure chambers of the elastic members 122a1 and 122a2 of the inner actuator 118A to the pressure chambers of the elastic members 122b1 and 122b2 of the outer actuator 118B. When the hydraulic oil is transferred into the pressure chambers of the elastic members 122b1 and 122b2 of the outer actuator 118B, the blocks 120b are pressed by the expanded elastic members 122b1 and 122b2, whereby actuator force is generated so as to apply bending force to the mounting portion 116, and supplementary muscular force for bending is transmitted to the joint of the user.

In order to transmit straightening force (supplementary muscular force) to the joint of the user, control is exerted so that hydraulic oil in the pressure chambers of the elastic members 122b1 and 122b2 of the outer actuator 118B is transferred to the pressure chambers in the elastic members 122a1 and 122a2 of the inner actuator 118A. When the hydraulic oil is transferred into the pressure chambers of the elastic members 112a1 and 122a2 of the inner actuator 118A, the block members 120a are pressed by the expanded elastic members 122a1 and 122a2, whereby actuator force is generated so as to apply straightening force to the mounting portion 116, and supplementary muscular force for straightening is transmitted to the joint of the user.

If trouble, such as oil leakage, occurs in a portion of the inner and outer actuators 118A and 118B, for example, when the pressure sensor 136a1 measures a low value, the generated-force stabilization control section 136d of the generated-force stabilizing section 136 outputs a signal for a closing operation to the control valve 136b1. This prevents all of the actuators from being disabled due to leakage of the hydraulic oil. Actuator force is thus generated by transferring the hydraulic oil among the pressure chambers in the elastic members 122a1 and 122a2 of the inner actuator 118A, the pressure chambers in the elastic members 122b1 and 122b2, and the reservoir 124.

The advantages of the muscular-force supplementing device 110 of this embodiment will now be described.

Since hydraulic oil in the reservoir 124, which is heated by the heater 126, is supplied to the inner actuator 118A and the outer actuator 118B, the mounting portion 116, to which heat is conducted from the hydraulic oil, does not become cold. Therefore, the user can comfortably wear the device in winter.

In the device 110, there are no actuators (artificial rubber muscles) which are not in close contact with the body, for example, as in the second conventional art, and the inner actuator 118A and the outer actuator 118B are simply placed along the outer periphery of the mounting portion 116. This makes it possible to provide an easily wearable device.

Even when the inner actuator 118A and the outer actuator 118B are partly faulty, the generated-force stabilizing section 136 separates the pressure chamber where oil leakage occurs, thereby preventing both the actuators from being disabled due to leakage of the hydraulic oil. Therefore, in a case in which the actuator breaks when the user is carrying something heavy, it is possible to prevent the joint from being damaged due to a sudden loss of supplementary muscular force.

Since the outer periphery of the mounting portion 116 is coated with the coating material 117 made of a high polymer capable of absorbing liquid, even if hydraulic oil leaks from the inner actuator 118A and the outer actuator 118B, the coating material 117 absorbs the oil and no oil will leak to the outside.

Since the muscular-force detector 138 is operated to obtain information about the muscle of the user by temporarily pressing the pushrod 138d against the skin of the user, problems, such as inflammation of the skin as in the first conventional art utilizing a myoelectric sensor, will not arise. Furthermore, the hydraulic-oil feeders 128a and 128b transfer hydraulic oil between the inner actuator 118A and the outer actuator 118B. The pressure chambers of the outer actuator 118B also serve as reservoirs when putting hydraulic oil into the pressure chambers of the inner actuator 118A, and the pressure chambers of the inner actuator 118A also serve as reservoirs when putting hydraulic oil into the pressure chambers of the outer actuator 118B. Therefore, no reservoir is necessary, or only a reservoir having a small capacity is necessary so as to supplement leakage of a small amount of hydraulic oil. This reduces the amount of hydraulic oil and allows a smaller and lighter device to be provided.

When transmitting supplementary muscular force for bending to the joint of the user, the adjoining blocks 120a of a plurality of blocks 120a in the inner actuator 118A contact so as to stop application of supplementary muscular force before the supplementary muscular force is excessively applied to the joint of the user. Therefore, it is possible to provide a muscular-force supplementing device with greater safety.

Figure 17:
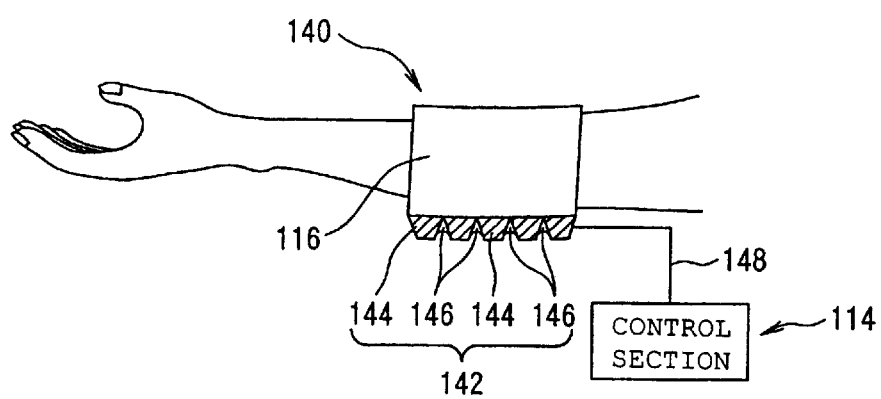
FIG. 17 is a view of a wearable muscular-force supplementing device according to a sixth embodiment of the present invention.

FIG. 17 shows a muscular-force supplementing device 140 according to a sixth embodiment, in which an actuator has a structure different from that of the fifth embodiment. The same components as those in the fifth embodiment are denoted by the same numerals, and descriptions thereof are omitted.

In the muscular-force supplementing device 140 of this embodiment, an outer actuator 142 is formed integrally with the outer periphery of a mounting portion 116.

The outer actuator 142 is driven by fluid pressure and includes a plurality of blocks 144 made of a hard material and fixedly arranged in the longitudinal direction of the mounting portion 116 at predetermined intervals, and a plurality of elastic members 146 placed in the spaces between the blocks 144.

The elastic members 146 have respective pressure chambers therein, are connected in serial to one another via oil paths formed in the blocks 144, and are connected to an oil path 148 extending to a control section 114.

When hydraulic oil flows into the pressure chambers of the elastic members 146, the elastic members 146 are expanded in the longitudinal direction so as to pressure the block members 144 and to apply bending force to the mounting portion 116. Supplementary muscular force for bending is thereby transmitted to the joint of the user. When hydraulic oil flows out of the pressure chambers of the elastic members 146, the elastic members 146 are contracted so as to remove the bending force applied to the mounting portion 116.

By forming the outer actuator 142 with the above structure integrally with the outer periphery of the mounting portion 116, it is possible to provide an easily wearable device having no actuator (artificial rubber muscle) which is not in close contact with the body, for example, as in the second conventional art.

When generating supplementary muscular force, the pressure chambers of the outer actuator 142 are pressed and hardened with some capacity. In this embodiment, since the actuator is placed outside, it does not hinder bending of the arm of the user and does not reduce the range of movement of the arm.

While the devices of the above-described embodiments apply supplementary muscular force to the wrist joint of the user, even when the present invention is applied to devices for applying supplementary muscular force to various joints of the body, such as an arm joint and a knee joint, similar functions and advantages can be obtained.

While hydraulic cylinders are used as the actuators in the embodiments, they may be replaced with pneumatic cylinders.

Furthermore, the number of the hydraulic-oil feeders 24a, 24b, and 24c in the first embodiment and the number of the actuator divisions 70 in the fourth embodiment are not limited to those mentioned in the embodiments.

As described above, in the wearable muscular-force supplementing device of the present invention, the controller includes the artificial muscular-force releasing device that releases the joint by stopping generation of supplementary muscular force in the artificial muscular-force generator. When the user assumes a dangerous attitude, for example, when the user is going to fall down, generation of supplementary muscular force in the artificial muscular-force generator is stopped, and the user can freely move the body without any restraint by the artificial muscular-force generator. Since the controller includes the generated-force stabilizer that restrains the force generated by the artificial muscular-force generator from being reduced due to breakage, even when the actuator breaks while the user is carrying something heavy, the generated-force stabilizer prevents the force generated by the actuator from being suddenly reduced.

The artificial muscular-force generator is electrically driven, there are provided two power sources, a main power source and an auxiliary power source, and the main power source and the auxiliary power source are connected to the power switching device. The power switching device performs switching so as to supply power from the auxiliary power source for a predetermined period when the power supply from the main power source is stopped. Since power is supplied from the auxiliary power source when the supply from the main power source is stopped, it is possible to avoid the danger of a sudden loss of supplementary muscular force.

The artificial muscular-force generator includes a pair of mounting portions to be worn at two positions on the body on both sides of the joint of the user, and an actuator connected between the mounting portions, wherein the actuator has the restraint device that prevents excessive supplementary muscular force from being applied to the joint of the user. This prevents the joint from being damaged due to excessive supplementary muscular force.

The artificial muscular-force generator includes a fluid-pressure type actuator that applies supplementary muscular force to the joint, and the heater is provided so as to heat fluid serving as a working fluid for the actuator to a predetermined temperature. This prevents the user from feeling uncomfortable, for example, feeling cold when wearing the device.

What is claimed is:

1. A wearable muscular-force supplementing device, comprising:

an artificial muscular-force generator that applied supplementary muscular force for bending to a joint of a user; and a controller that controls driving of said artificial muscular-force generator, said controller having an artificial msucular-force releasing device that releases the joint from restraint by stopping generation of supplementary muscular force by said artifical muscular-force generator, wherein said artificial muscular-force releasing device has a sensor that detects an attitude of the user, and a release controller that stops generation of supplementary muscular force by said artificial muscular-force generator when determining, based on information detected by said sensor, that the user is in a dangerous attitude.

2. The wearable muscular-force supplementing device according to claim 1, wherein said controller has a voice input device and controls generation of supplementary muscualr force to be applied to the joint by said artificial muscular-force generator or exerts control so as to operate said artificial muscular-force releasing device, based on voice input from said voice input device.

3. The wearable muscular-force supplementing device according to claim 1, wherein said artificial muscular-force generator has a fluid-pressure type actuator, said controller includes a reservoir that stores fluid, a fluid feeding device that pressurizes and transfers the fluid received from said reservoir to said actuator, and a feeding-drive control device that controls said fluid feeding device, said artififcial muscular-force releasing device has a control valve interposed in a fluid path communicating with said actuator and connected to said reservoir while detouring around said fluid feeding device, and said release controller has an opening control section that controls the opening of said control valve.

4. The wearable muscular-force supplementing device according to claim 1, further comprising:

said artificial muscular-force generator being electrically driven;

a power switching mechanism; and power sources including a main power source and an auxiliary power source, said main power source and said auxiliary power source being connected to the power switching device, said power switching device performing switching so as to supply power from said auxiliary power source for a predetermined time when power supply from said main power source is stopped.

5. The wearable muscular-force supplementing device according to claim 4, wherein said power switching device has an alarm device that sounds an alarm when power supply from said auxiliary power source is started.

6. A wearable muscular-force supplementing device according to claim 1, further comprising:

said artificial muscular-force generator having a pair of mounting portions to be worn at two positions on the body of the user on both sides of the joint, and an actuator connected between said mounting portions, said actuator having a restraint that prevents excessive supplementary muscular force from being applied to the joint of the user.

7. The wearable muscular-force supplementing device according to claim 6, wherein said restraint is formed by placing stopper members opposed to each other in said mounting portions so that the positions thereof are adjustable and so that said stopper members contact before excessive supplementary muscular force is applied to the joint of the user.

8. The wearable muscular-force supplementing device according to claim 6, wherein said restraint is formed by connecting a variable-length elastic belt between said mounting portions so that the force of said actuator is stopped by tension generated by said elastic belt before excessive supplementary muscular force is applied to the joint of the user.

9. A wearable muscular-force supplementing device according to claim 1, further comprising:
said artificial muscular-force generator having a fluid-pressure type actuator having a pressure chamber; and
said controller including a fluid transfer control section that controls transfer of the fluid with respect to said actuator, at least one of said actuator and said fluid transfer control section having a fluid discharge control section that discharges internal fluid to the exterior of the device.

10. The wearable muscular-force supplementing device according to claim 9, wherein said fluid discharge control section has a leakage alarm that detects leakage of the fluid and sounds an alarm when discharge of the fluid out of at least said actuator and said fluid transfer control section is stopped.

11. The wearable muscular-force supplementing device according to claim 9, wherein said controller includes a fluid supply control section capable of supplying the fluid from an exterior of the device to at least one of said actuator and said fluid transfer control section, and a filter placed at an inlet of said fluid supply control section so as to remove foreign matters mixed in the fluid.

12. A wearable muscular-force supplementing device according to claim 1, further comprising:
said controller being driven by power from an external power source, and having a power cord to be connected to said external power source, and a cord reel that winds up said power cord.

13. The wearable muscular-force supplementing device according to claim 12, wherein said cord reel is worn on the body of the user via a holder, and said holder has a mechanism that allows a cord-dispensing hole of said cord reel to freely point upward, downward, rightward, and leftward.

14. The wearable muscular-force supplementing device according to claim 13, wherein said controller has a power cord alarm that sounds an alarm when it is determined that the length of said power cord remaining in said cord reel is less than a predetermined length.

15. A wearable muscular-force supplementing device, comprising;
an artificial muscular-force generator that applies supplementary muscular force for bending to a joint of a user; wherein said artificial muscular-force generator includes a fluid-pressure type actuator having a plurality of pressure chambers and,
a controller that controls driving of said artificial muscular-force generator, said controller having a generated-force stabilizer that separates said pressure chambers and inhibits force generated by said artificial muscular-force generator from being reduced due to failure of the artificial muscular force generator.

16. The wearable muscular-force supplementing device according to claim 15, wherein said controller includes a reservoir that stores fluid, a fluid feeding device that pressurizes and transfers the fluid received from said reservoir to said actuator, and a feeding-drive control device that controls said fluid feeding device, and said generated-force stabilizer includes a pressure sensor that detects the pressures in said pressure chambers, control valves interposed in a plurality of flow paths connected between said fluid feeding device and said pressure chambers of said actuator, and a generated-force stabilization control section that closes a control valve connected to a given pressure chamber when it is determined based on information detected by said pressure sensor that the pressure in said pressure chamber is decreased.

17. A wearable muscular-force supplementing device, comprising:
an artificial muscular-force generator that applies supplementary muscular force for bending to a joint of a user, said artificial muscular-force generator having a pair of mounting portions to be worn at two positions on the body of the user on both sides of the joint, and an actuator connected between said mounting portions, said actuator including a plurality of actuator divisions arranged in parallel and connected to one another between said mounting portions, said mounting portions having detachably connecting portions that detachably connect said actuator divisions thereto and a predetermined number of said actuator divisions are connected to said detachably connecting portions of said mounting portions in accordance with a desired power of supplementary muscular force; said predetermined number of actuator divisions being mounted in parallel; and
a controller that controls driving of said artificial muscular-force generator.

18. The wearable muscular-force supplementing device according to claim 17, wherein said actuator divisions are formed of fluid-pressure type actuators, each having a pressure chamber therein, and said detachably connecting portions of said mounting portions also serve as fluid transfer connectors that transfer fluid serving as working fluid into and out of said pressure chambers of said actuator divisions.

19. A wearable muscular-force supplementing device, comprising:
an artificial muscular-force generator that applies supplementary muscular force for bending to a joint of a user, said artificial muscular-force generator having a flexible mounting portion that is cylindrically shaped so as to wrap the joint of the user in close contact therewith, and a fluid-pressure type actuator formed integrally and parallel with an outer periphery of said mounting portion so as to apply supplementary muscular force to the joint while bending said mounting portion; and
a controller that controls driving of said artificial muscular-force generator wherein said controller has a heating device that heats fluid serving as working fluid for said actuator to a predetermined temperature.

20. The wearable muscular-force supplementing device according to claim 19, wherein said mounting portion is provided with a muscular force detector that measures muscular force based on pressing force temporarily applied to the skin of the user, and said controller controls supplementary muscular force generated by said actuator based on muscular force information obtained from said muscular force detector.

21. A wearable muscular-force supplementing device according to claim 20, wherein said muscular force detector includes a driving motor, a transmission mechanism that transmits rotating force of said driving motor as linear motion to a pushrod, and a torque measuring instrument that measures the torque value of said driving motor when the skin is pushed by said pushrod and outputs the torque value as the pressing force to said controller.

22. The wearable muscular-force supplementing device according to claim 19, wherein said actuator includes an inner actuator placed on the inner side of the joint, extending in the longitudinal direction of the outer periphery of said mounting portion, and having a pressure chamber made of an elastic material, and an outer actuator placed on the outer side of the joint, extending in the longitudinal direction of the outer periphery of said mounting portion, and having a pressure chamber made of an elastic material.

23. The wearable muscular-force supplementing device according to claim 22, wherein said inner and outer actuators each have a plurality of convex members fixed on the outer periphery of said mounting portion with a predetermined space therebetween in the longitudinal direction, and a plurality of elastic members placed in the spaces between said convex members, each of said elastic members being expanded and contracted in response to the inflow and outflow of fluid into and from said pressure chamber formed therein, and each of said convex members being pressed by expansion of said elastic member so as to apply bending force to said mounting portion.

24. The wearable muscular-force supplementing device according to claim 22, wherein said controller exerts control so as to transfer fluid between said pressure chambers of said elastic members constituting said inner actuator and said pressure chambers of said elastic members constituting said outer actuator.

25. The wearable muscular-force supplementing device according to claim 19, wherein said actuator includes an outer actuator placed on the outer side of the joint, extending in the longitudinal direction of the outer periphery of said mounting portion, and having a pressure chamber made of an elastic material, and the outer actuator being expanded in the longitudinal direction in response to the inflow of the fluid into said pressure chamber so as to apply bending force to said mounting portion, and being contracted in response to the outflow of the fluid from said pressure chamber so as to release the bending force on said mounting portion.

26. The wearable muscular-force supplementing device according to claim 25, wherein said outer actuator includes a plurality of convex members fixed on the outer periphery of said mounting portion with a predetermined space therebetween in the longitudinal direction, and a plurality of elastic members placed in the spaces between said convex members, said elastic members being expanded in the longitudinal direction in response to the inflow of the fluid in said pressure chamber formed therein so as to press said convex members and to apply bending force to said mounting portion.

27. The wearable muscular-force supplementing device according to claim 19, wherein said controller has a generated-force stabilizer that inhibits the force generated by said artificial muscular-force generator from being reduced due to breakage.

28. The wearable muscular-force supplementing device according to claim 23, wherein said convex members function as stopper members that stop application of supplementary muscular force by contacting with one another before excessive supplementary muscular force is applied to the joint of the user.

29. The wearable muscular-force supplementing device according to claim 19, wherein said fluid is liquid, and the outer periphery of said mounting portion is coated with a periphery-coating member having a liquid absorbing function.

30. A wearable muscular-force supplementing device, comprising:

an artificial muscular-force generator that applies supplementary muscular force for bending to a joint of a user; and a controller that controls driving of said artificial muscular-force generator, said controller having an artificial muscular-force releasing device that releases the joint from restraint by stopping generation of supplementary muscular force by said artificial muscular-force generator;

wherein said artificial muscular-force releasing device has a sensor that detects an attitude of the user, and a release controller that stops generation of supplementary muscular force by said artificial muscular-force generator when determining, based on information detected by said sensor, that the user is in a dangerous attitude; and wherein said controller has a voice input device and controls generation of supplementary muscular force to be applied to the joint by said artificial muscular-force generator or exerts control so as to operate said artificial muscular-force releasing device, based on voice input from said voice input device.

31. A wearable muscular-force supplementing device, comprising:

an artificial muscular-force generator that applies supplementary muscular force for bending to a joint of a user, said artificial muscular-force generator having a flexible mounting portion that is cylindrically shaped so as to wrap the joint of the user in close contact therewith, and a fluid-pressure type actuator formed integrally with an outer periphery of said mounting portion so as to apply supplementary muscular force to the joint while bending said mounting portion; and a controller that controls driving of said artificial muscular-force generator;

wherein said actuator includes an outer actuator placed on the outer side of the joint, extending in the longitudinal direction of the outer periphery of said mounting portion, and having a pressure chamber made of an elastic material, and the outer actuator being expanded in the longitudinal direction in response to the inflow of the fluid into said pressure chamber so as to apply bending force to said mounting portion, and being contracted in response to the outflow of the fluid from said pressure chamber so as to release the bending force on said mounting portion;

wherein said outer actuator includes a plurality of convex members fixed on the outer periphery of said mounting portion with a predetermined space therebetween in the longitudinal direction, and a plurality of elastic members placed in the spaces between said convex members, said elastic members being expanded in the longitudinal direction in response to the inflow of the fluid in said pressure chamber formed therein so as to press said convex members and to apply bending force to said mounting portion; and wherein said convex members function as stopper members that stop application of supplementary muscular force by contacting with one another before excessive supplementary muscular force is applied to the joint of the user.

* * * * *